(12) United States Patent
Lu et al.

(10) Patent No.: US 9,981,915 B2
(45) Date of Patent: May 29, 2018

(54) COMPOUNDS FOR TREATMENT OF CANCER

(71) Applicants: GTx, Inc., Memphis, TN (US); UNIVERSITY OF TENNESSEE RESEARCH FOUNDATION, Knoxville, TN (US)

(72) Inventors: Yan Lu, Bartlett, TN (US); James T Dalton, Ann Arbor, MI (US); Wei Li, Germantown, TN (US); Duane D Miller, Collierville, TN (US)

(73) Assignees: UNIVERSITY OF TENNESSEE RESEARCH FOUNDATION, Knoxville, TN (US); GTx, INC, Memphis, TN (US)

( * ) Notice: Subject to any disclaimer, the term of this patent is extended or adjusted under 35 U.S.C. 154(b) by 0 days. days.

(21) Appl. No.: 15/309,357

(22) PCT Filed: May 5, 2015

(86) PCT No.: PCT/US2015/029270
§ 371 (c)(1),
(2) Date: Nov. 7, 2016

(87) PCT Pub. No.: WO2015/171628
PCT Pub. Date: Nov. 12, 2015

(65) Prior Publication Data
US 2017/0057930 A1  Mar. 2, 2017

Related U.S. Application Data

(60) Provisional application No. 61/989,294, filed on May 6, 2014.

(51) Int. Cl.
| | |
|---|---|
| *C07D 401/02* | (2006.01) |
| *C07D 401/10* | (2006.01) |
| *C07D 401/14* | (2006.01) |
| *A61K 31/437* | (2006.01) |
| *A61K 31/4353* | (2006.01) |
| *C07D 235/18* | (2006.01) |
| *A61K 31/4184* | (2006.01) |
| *C07D 403/04* | (2006.01) |
| *C07D 417/12* | (2006.01) |
| *C07D 471/04* | (2006.01) |
| *C07D 277/24* | (2006.01) |
| *A61K 31/426* | (2006.01) |
| *A61K 45/06* | (2006.01) |

(52) U.S. Cl.
CPC ........ *C07D 235/18* (2013.01); *A61K 31/4184* (2013.01); *A61K 31/426* (2013.01); *A61K 31/437* (2013.01); *A61K 45/06* (2013.01); *C07D 277/24* (2013.01); *C07D 403/04* (2013.01); *C07D 417/12* (2013.01); *C07D 471/04* (2013.01)

(58) Field of Classification Search
CPC .. C07D 401/02; C07D 401/10; C07D 401/14; A61K 31/437; A61K 31/4353
USPC .......................... 546/119, 121; 514/303, 300
See application file for complete search history.

(56) References Cited

U.S. PATENT DOCUMENTS

| | | | |
|---|---|---|---|
| 8,822,513 | B2 | 9/2014 | Lu et al. |
| 9,029,408 | B2 | 5/2015 | Miller et al. |
| 9,334,242 | B2 | 5/2016 | Lu et al. |
| 9,447,049 | B2 | 9/2016 | Li et al. |
| 2004/0267017 | A1 | 12/2004 | Bierer et al. |
| 2006/0189618 | A1 | 8/2006 | Pelletier |
| 2006/0252793 | A1 | 11/2006 | Ameriks et al. |
| 2008/0125418 | A1 | 5/2008 | Babin et al. |
| 2009/0326020 | A1 | 12/2009 | Miller et al. |
| 2011/0257196 | A1 | 10/2011 | Lu et al. |
| 2012/0196879 | A1 | 8/2012 | Dumble et al. |
| 2013/0297049 | A1 | 11/2013 | Morita |

FOREIGN PATENT DOCUMENTS

| | | |
|---|---|---|
| WO | WO 2004/052280 A2 | 6/2004 |
| WO | WO 2010/074776 | 7/2010 |
| WO | WO 2011/047238 A1 | 4/2011 |
| WO | WO 2011/109059 A1 | 9/2011 |

OTHER PUBLICATIONS

Lu et al., Journal of Medicinal Chemistry (2014), 57(17), 7355-7366.*
Bellina, F et al., Novel imidazole-based combretastatin A-4 analogues: Evaluation of their in vitro antitumor activity and molecular modeling study of their binding to the colchicine site of tubulin, Bioorganic & Medicinal Chemistry Letters 16, pp. 5757-5762, 2006.
International Search Report dated Sep. 21, 2015.
Office Action and English translation issued for Chinese application No. 201480025267.4 dated Oct. 21, 2016.
Supplementary Partial European Search Report Corresponding to EP patent No. 2964028 dated Dec. 14, 2016.
Supplementary European Search Report Corresponding to EP patent No. 2964028 dated May 9, 2017.
Sapna P. Patel et al: "Clinical responses to selumetinib (AZD6244; ARRY-142886)-based combination therapy stratified by gene mutations in patients with metastatic melanoma", Cancer. ,vol. 119, No. 4, Sep. 12, 2012 (Sep. 12, 2012), pp. 799-805.
N. K. Haass et al: liThe Mitogen-Activated Protein/Extracellular Signal-Regulated Kinase Kinase Inhibitor AZD6244 (ARRY-142886) Induces Growth Arrest in Melanoma Cells and Tumor Regression When Combined with Docetaxel, Clinical Cancer Research, vol. 14, No. 1. Jan. 1, 2008 (Jan. 1, 2008), pp. 230-239.
Anna Tesei et al: II Low-dose taxotere enhances the ability of sorafenib to induce apoptosis in gastric cancer models. Journal of Cellular and Molecular Medicine. vol. 15. No. 2. Feb. 1, 2011 (Feb. 1, 2011). pp. 316-326.

(Continued)

*Primary Examiner* — Niloofar Rahmani
(74) *Attorney, Agent, or Firm* — Mark S. Cohen; Pearl Cohen Zedek Latzer Baratz LLP

(57) ABSTRACT

The present invention relates to colchicine-binding site compounds having anti-cancer activity, compositions comprising the same, and their use for treating various forms of cancer.

7 Claims, 6 Drawing Sheets

(56) References Cited

OTHER PUBLICATIONS

Lucy Lee et al., The safety, tolerability, pharmacokinetics, and pharmacodynamics of single oral doses of RO5068760, an MEK inhibitor, in healthy volunteers: assessment of target suppression *J Clin Pharmacol*, No. 50.(Dec. 31, 2010) pp. 1397-1405.
R. N. Amaria et al: "Therapeutic options in cutaneous melanoma: latest developments". Therapeutic Advances in Medical Oncologyenglandjan 2016. vol. 3. No. 5. Sep. 1, 2011 (Sep. 1, 2011). pp. 245-251.
Jianjun Chen et al: "Discovery of Novel 2-Aryl-4-benzoyl-imidazole (AbI-III) Analogues Targeting Tubulin Polymerization as Antiproliferative Agents". Journal of Medicinal Chemistry. vol. 55. No. 16. Aug. 23, 2012 (Aug. 23, 2012). pp. 7285-7289.
Zhao Wang et al: "Novel Tubulin Polymerization Inhibitors Overcome Multidrug Resistance and Reduce Melanoma Lung Metastasis". Pharmaceutical Research. Kluwer Academic Publishers—Plenum Publishers. NL. vol. 29. No. 11. Mar. 13, 2012 (Mar. 13, 2012). pp. 3040-3052.
Chien-Ming Li et al: "Orally Bioavailable Tubulin Antagonists for Paclitaxel Refractory Cancer". Pharmaceutical Research. Kluwer Academic Publishers-Plenum Publishers. NL. vol. 29. No. 11.Jul. 4, 2012 (Jul. 4, 2012). pp. 3053-3063.
J. Wang et al: "Synergistic Combination of Novel Tubulin Inhibitor ABI-274 and Vemurafenib Overcomes Vemurafenib Acquired Resistance in BRAFV600E Melanoma". Molecular Cancer Therapeutics. vol. 13. No. 1. Nov. 18, 2013 (Nov. 18, 2013). pp. 16-26.
Greg Barsh et al: "XVIII PASPCR 2013 Advances in Melanocyte and Melanoma Biology President Local Organizing Committee Past-President and IFPCS Representative", UW Hospital & Clinics, Sep. 1, 2013 (Sep. 1, 2013).
Office Action and English translation issued for Chinese application No. 201480025267.4 dated Jun. 20, 2017.
Office Action for corresponding U.S. Appl. No. 14/773,265 dated Feb. 2, 2017.
Office Action for Israel application No. 239672 dated Dec. 9 2016.
Office Action for corresponding European application No. 10 847 161.6 dated Feb. 6, 2017.
Khalili B et al: "Novel one-pot synthesis of (4 or 5)-aryl-2-aryloyl (1 H)-imidazoles in water and tanto-isomerization study using NMR", Tetrahedron, vol. 65, No. 34, Aug. 22, 2009, pp. 6882-6887.
Schubert H et al: "N-Alkyl-Uno N-Alkoxyderivate Des 3-Hydroxy-2,5 Diphenyl-Pyrazine", Journal Fuer Praktische Chemie (Leipzig) vol. 33, 1966, pp. 265-276.
Schubert et al: "Phasenbeziehungen zwischen Imidazolylketonen und Hydroxypyrazinen", Journal Fuer Praktische Chemie (Leipzig) vol. 24, 1964, pp. 125-130.
Schubert et al: "Kristallin-flussige Hydroxypyrazine", Zeitschrift Fuer Chemie (Stuttgart) vol. 4, 1964, p. 228.
Office Action for corresponding European application No. 10 847 161.6 dated Jul. 20, 2017.
Office Action for corresponding Canadian application No. 2,791,138 dated Mar. 31, 2017.
Tucker, J. A. et al., "Structure-Activity Relationships of Acyloxyamidine Cytomegalovirus DNA Polymerase Inhibitors", Bloorganic and Medicinal Chemistry, 8, pp. 601-615, 2000.
Terasawa, K. et al., "Cytotoxic Activity of 5-Benzoylimidazole and Related Compounds against Human Oral Tumor Cell Lines", Anti-cancer Research, 21, pp. 1081-1086, 2001.
Mahboobi, S. et al., "Synthesis of Naturally Occurring Pyrazine and Imidazole Alkaloids from Botryllus", Monatshefte for Chemie, 135, pp. 333-342, 2004 Canada.
Office Action and English translation issued for Chinese application No. 201410828197.8 dated Feb. 20, 2017.
Office Action and English translation issued for Korean application No. 10-2016-7017425 dated Feb. 3, 2017.
Extended European Search Report Corresponding to EP patent No. 15789404.0 dated Dec. 8, 2017.
Yan Lu et al., "An Overview of Tubulin Inhibitors that Interact with the Colchicine Binding Site" Pharm Res 2012 pp. 2943-2971 Published online Jul. 20, 2017 Springer Science + Business Media, LLC.

\* cited by examiner

US 9,981,915 B2

COMPOUNDS FOR TREATMENT OF CANCER

PRIORITY CLAIM

This application is a 371 of International Patent Application No. PCT/2015/029270, filed May 5, 2015, which, in turn, claims priority of U.S. Provisional Application No. 61/989,294, filed May 6, 2014.

GOVERNMENT INTEREST STATEMENT

This invention was made in whole or in part with government support by the Van Vleet Endowed Professorship (D.D.M.), and NIH (National Institutes of Health) grant R01CA148706, 1S10RR026377-01, 1S10OD010678-01 (W.L.). The U.S. government has certain rights in this invention.

FIELD OF THE INVENTION

The present invention relates to colchicine-binding site compounds having anti-cancer activity, compositions comprising the same, and their use for treating various forms of cancer.

BACKGROUND OF THE INVENTION

Cancer is the second most common cause of death in the United States, exceeded only by heart disease. In the United States, cancer accounts for 1 of every 4 deaths. The 5-year relative survival rate for all cancers patients diagnosed in 1996-2003 is 66%, up from 50% in 1975-1977 (*Cancer Facts & Figures* American Cancer Society: Atlanta, Ga. (2008)). This improvement in survival reflects progress in diagnosing at an earlier stage and improvements in treatment. Discovering highly effective anticancer agents with low toxicity is a primary goal of cancer research.

Prostate cancer is one of the most frequently diagnosed noncutaneous cancers among men in the US and is the second most common cause of cancer deaths with over 180,000 new cases and almost 29,000 deaths expected this year. Patients with advanced prostate cancer undergo androgen deprivation therapy (ADT), typically either by luteinizing hormone releasing hormone (LHRH) agonists or by bilateral orchiectomy. Androgen deprivation therapy not only reduces testosterone, but estrogen levels are also lower since estrogen is derived from the aromatization of testosterone, which levels are depleted by ADT. Androgen deprivation therapy-induced estrogen deficiency causes significant side effects which include hot flushes, gynecomastia and mastalgia, bone loss, decreases in bone quality and strength, osteoporosis and life-threatening fractures, adverse lipid changes and higher cardiovascular disease and myocardial infarction, and depression and other mood changes.

Malignant melanoma is the most dangerous form of skin cancer, accounting for about 75% of skin cancer deaths. The incidence of melanoma is rising steadily in Western populations. The number of cases has doubled in the past 20 years. Around 160,000 new cases of melanoma are diagnosed worldwide each year, and it is more frequent in males and Caucasians. According to a WHO Report, about 48,000 melanoma-related deaths occur worldwide per year.

Currently there is no effective way to treat metastatic melanoma. It is highly resistant to current chemotherapy, radiotherapy, and immunotherapy. Metastatic melanoma has a very poor prognosis, with a median survival rate of 6 months and a 5-year survival rate of less than 5%. In the past 30 years, dacarbazine (DTIC) is the only FDA-approved drug for metastatic melanoma. However, it provides only less than 5% of complete remission in patients. In recent years, great efforts have been attempted in fighting metastatic melanoma. Neither combinations of DTIC with other chemotherapy drugs (e.g., cisplatin, vinblastine, and carmustine) nor adding interferon-α2b to DTIC have shown a survival advantage over DTIC treatment alone. Most recently, clinical trials with antibodies and vaccines to treat metastatic melanoma also failed to demonstrate satisfactory efficacy. Ipilimumab (Yervoy) is such a drug that uses your immune system to fight melanoma. Ipilimumab is used to treat advanced melanoma that has spread beyond its original location. Targeted therapy uses medications designed to target specific vulnerabilities in cancer cells. Vemurafenib (Zelboraf) is a targeted therapy approved to treat advanced melanoma that cannot be treated with surgery or melanoma that has spread through the body. Vemurafenib only treats melanoma that has a certain genetic mutation.

Tubulin/microtubule-interacting drugs are used successfully for treatment of a wide variety of human cancers. They are commonly classified into two major categories: microtubule-stabilizing (e.g., taxanes, epothilones) and microtubule-destabilizing drugs (e.g., vinca alkaloids, colchicine). Three major binding sites on α,β-tubulin subunits have been identified as taxane-, vinca alkaloid- and colchicine-binding sites. While antimitotic agents interacting with the taxane- or vinca alkaloid-binding sites in tubulin are tremendously successful in clinical oncology, there are no Food and Drug Administration (FDA)-approved colchicine-binding site drugs currently available for cancer treatment. Most of the colchicine-binding agents have high potency, relatively simple chemical structures for optimization, selective toxicity towards tumor vasculature, and show promising ability to overcome P-glycoprotein (P-gp) efflux pump mediated multidrug resistance.

Several outstanding agents for such an approach are listed in FIG. 1. Combretastatin A-4 (CA-4) is the most active member of the combretastatins family, isolated from the African tree *Combretum caffrum*. CA-4 exhibits strong antitubulin activity by binding to the colchicine-site and has been the subject of Phase II and Phase III clinical studies. The replacement of the olefinic bridge of CA-4 with a carbonyl group yields phenstatin, which has similar potency and mechanisms of action with CA-4. BPR0L075 and Oxi-6196 are 2-aroylindole and dihydronaphthalene analogues of CA-4, which show strong inhibition on tubulin polymerization. Methylated chalcone SD400, which has an $IC_{50}$ value of 0.21 nM against K562 human leukemia cells, is a potent tubulin inhibitor. Podophyllotoxin is a non-alkaloid toxin lignin, and it also possesses an anticancer property that can be attributed to the inhibition of tubulin polymerization through binding to the colchicine binding site. Accordingly, the colchicine-binding site compounds have attracted great interest from medicinal chemists in recent years.

SUMMARY OF THE INVENTION

In one embodiment, this invention is directed to a compound represented by formula II:

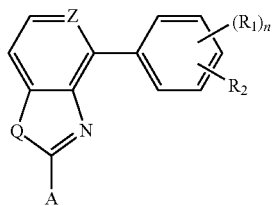

(II)

wherein
Q is S, NH, or O;
Z is CH or N;
A is substituted or unsubstituted phenyl; substituted or unsubstituted indolyl; or substituted or unsubstituted indazolyl;
wherein the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_i$ $NH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;
$R_1$ is independently hydrogen, O-alkyl, O-haloalkyl, F, Cl, Br, I, haloalkyl, $CF_3$, CN, $NO_2$, —$CH_2CN$, $NH_2$, hydroxyl, COOH, C(O)H, NHCO-alkyl, —$O(CH_2)_j$ $OCH_3$, —$O(CH_2)_jOH$, —$O(CH_2)_jNHCH_3$, —$O(CH_2)_j$ $NH_2$, —O—$(CH_2)_jN(CH_3)_2$, —$OC(O)CF_3$, —OC(O) $CH_2Cl$, —$OCH_2Ph$, —$O(CH_2)_jNH_2$, —$O(CH_2)_j$N-phthalimide or a combination thereof;
$R_2$ is hydrogen, O-alkyl, O-haloalkyl, F, Cl, Br, I, haloalkyl, $CF_3$, CN, $NO_2$, —$CH_2CN$, $NH_2$, hydroxyl, COOH, C(O)H, NHCO-alkyl, —$O(CH_2)_kOCH_3$, —$O(CH_2)_kOH$, —$O(CH_2)_kNHCH_3$, —$O(CH_2)_kNH_2$, —O—$(CH_2)_kN(CH_3)_2$, —$OC(O)CF_3$, —OC(O) $CH_2Cl$, —$OCH_2Ph$, —$O(CH_2)_kNH_2$ or —$O(CH_2)_k$N-phthalimide;
i, j, and k are independently an integer between 0 to 5;
n is an integer between 1 to 4;
or a metabolite, hydrate, isomer, N-oxide, prodrug, pharmaceutical product, pharmaceutically acceptable salt, polymorph, tautomer, or a combination thereof.

In one embodiment, this invention is directed to a compound represented by formula XII:

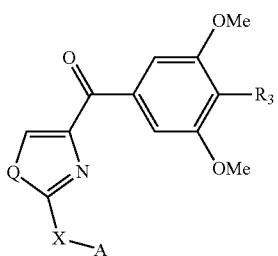

(XII)

wherein
Q is S, NH or O;
X is a bond or NH;
A is substituted or unsubstituted phenyl; substituted or unsubstituted indolyl; or substituted or unsubstituted indazolyl;
wherein the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_i$ $NH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;
$R_3$ is hydrogen, O-alkyl, O-haloalkyl, F, Cl, Br, I, $NO_2$, haloalkyl, $CF_3$, CN, —$CH_2CN$, $NH_2$, hydroxyl, —$O(CH_2)_o$ $NHCH_3$, —$O(CH_2)_oNH_2$, —$O(CH_2)_oN(CH_3)_2$, —$O(CH_2)_o$ OMe, —$O(CH_2)_oOH$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H or —$C(O)NH_2$;
i and o are independently an integer between 0 to 5;
or a metabolite, hydrate, isomer, N-oxide, prodrug, pharmaceutical product, pharmaceutically acceptable salt, polymorph, tautomer, or a combination thereof.

In one embodiment, this invention is directed to a pharmaceutical composition of this invention. In another embodiment, this invention is directed to a pharmaceutical composition of this invention and at least one pharmaceutically active compound useful in the treatment of cancer.

In one embodiment, this invention is directed to a method of treating, suppressing, reducing the severity, reducing the risk, or inhibiting cancer comprising administering a compound of this invention to a subject having cancer under conditions effective to treat the cancer. In another embodiment, the cancer is selected from the group consisting of prostate cancer, drug-resistant prostate cancer, breast cancer, drug-resistant breast cancer, ovarian cancer, drug-resistant ovarian cancer, skin cancer, melanoma, drug-resistant melanoma, lung cancer, colon cancer, glioma, leukemia, lymphoma, renal cancer, CNS cancer, uterine cancer, drug-resistant uterine cancer, and combinations thereof. In another embodiment, the administering of the compound of this invention is carried out in combination with another cancer therapy.

In one embodiment, this invention is directed to a method of treating a drug resistant tumor or tumors comprising administering a compound of this invention to a subject suffering from cancer under conditions effective to treat the drug resistant tumor or tumors. In another embodiment, the cancer is selected from the group consisting of prostate cancer, drug-resistant prostate cancer, breast cancer, drug-resistant breast cancer, ovarian cancer, drug-resistant ovarian cancer, skin cancer, melanoma, drug-resistant melanoma, lung cancer, colon cancer, glioma, leukemia, lymphoma, renal cancer, CNS cancer, uterine cancer, drug-resistant uterine cancer, and combinations thereof. In another embodiment, the administering of the compound of this invention is carried out in combination with another cancer therapy.

Other features and advantages of the present invention will become apparent from the following detailed description, examples, and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
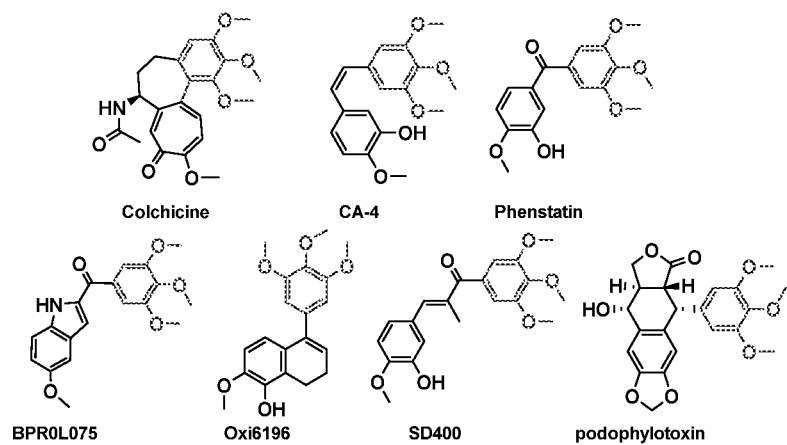
FIG. 1 depicts structures of representative tubulin inhibitors that bind to the colchicine-binding site.

In one embodiment, this invention is directed to a compound of formula (I)

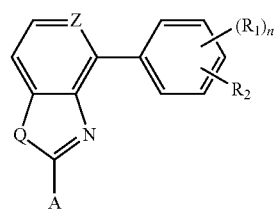

(I)

wherein
Q is S, NH, or O;
Z is CH or N;
A is substituted or unsubstituted phenyl; substituted or unsubstituted indolyl; or substituted or unsubstituted indazolyl;
wherein the optional substituents of A include O-alkyl, O-haloalkyl, F, Cl, Br, I, $NO_2$, haloalkyl, $CF_3$, CN, $-CH_2CN$, $NH_2$, hydroxyl, $-(CH_2)_iNHCH_3$, $-(CH_2)_i NH_2$, $-(CH_2)_iN(CH_3)_2$, $-OC(O)CF_3$, $-SO_2$-aryl, $C_1$-$C_5$ linear or branched alkyl, haloalkyl, alkylamino, aminoalkyl, $-OCH_2Ph$, $-NHCO$-alkyl, COOH, $-C(O)Ph$, $C(O)O$-alkyl, $C(O)H$, $-C(O)NH_2$ or a combination thereof;

wherein
Q is S, NH, or O;
Z is CH or N;
A is substituted or unsubstituted single-, fused- or multiple-ring aryl or (hetero)cyclic ring systems, including saturated and unsaturated N-heterocycles, saturated and unsaturated S-heterocycles, and saturated and unsaturated O-heterocycles, saturated or unsaturated cyclic hydrocarbons, saturated or unsaturated mixed heterocycles, aliphatic straight- or branched-chain $C_1$ to $C_{30}$ hydrocarbons;
wherein the optional substituents of A include O-alkyl, O-haloalkyl, F, Cl, Br, I, $NO_2$, haloalkyl, $CF_3$, CN, $-CH_2CN$, $NH_2$, hydroxyl, $-(CH_2)_iNHCH_3$, $-(CH_2)_i NH_2$, $-(CH_2)_iN(CH_3)_2$, $-OC(O)CF_3$, $-SO_2$-aryl, $C_1$-$C_5$ linear or branched alkyl, haloalkyl, alkylamino, aminoalkyl, $-OCH_2Ph$, $-NHCO$-alkyl, COOH, $-C(O)Ph$, $C(O)O$-alkyl, $C(O)H$, $-C(O)NH_2$ or a combination thereof;
$R_1$ is independently hydrogen, O-alkyl, O-haloalkyl, F, Cl, Br, I, haloalkyl, $CF_3$, CN, $NO_2$, $-CH_2CN$, $NH_2$, hydroxyl, COOH, $C(O)H$, NHCO-alkyl, $-O(CH_2)_j OCH_3$, $-O(CH_2)_j OH$, $-O(CH_2)_j NHCH_3$, $-O(CH_2)_j NH_2$, $-O-(CH_2)_j N(CH_3)_2$, $-OC(O)CF_3$, $-OC(O)CH_2Cl$, $-OCH_2Ph$, $-O(CH_2)_j NH_2$, $-O(CH_2)_j$N-phthalimide or a combination thereof;
$R_2$ is hydrogen, O-alkyl, O-haloalkyl, F, Cl, Br, I, haloalkyl, $CF_3$, CN, $NO_2$, $-CH_2CN$, $NH_2$, hydroxyl, COOH, $C(O)H$, NHCO-alkyl, $-O(CH_2)_k OCH_3$, $-O(CH_2)_k OH$, $-O(CH_2)_k NHCH_3$, $-O(CH_2)_k NH_2$, $-O-(CH_2)_k N(CH_3)_2$, $-OC(O)CF_3$, $-OC(O)CH_2Cl$, $-OCH_2Ph$, $-O(CH_2)_k NH_2$ or $-O(CH_2)_k$N-phthalimide;
i, j, and k are independently an integer between 0 to 5;
n is an integer between 1 to 4;
or a metabolite, hydrate, isomer, N-oxide, prodrug, pharmaceutical product, pharmaceutically acceptable salt, tautomer, polymorph or a combination thereof.

In one embodiment, this invention is directed to a compound of formula (II)

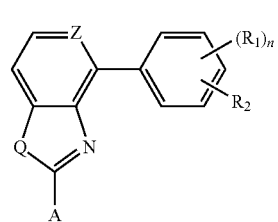

(II)

R₁ is independently hydrogen, O-alkyl, O-haloalkyl, F, Cl, Br, I, haloalkyl, CF₃, CN, NO₂, —CH₂CN, NH₂, hydroxyl, COOH, C(O)H, NHCO-alkyl, —O(CH₂)ⱼOCH₃, —O(CH₂)ⱼOH, —O(CH₂)ⱼNHCH₃, —O(CH₂)ⱼNH₂, —O—(CH₂)ⱼN(CH₃)₂, —OC(O)CF₃, —OC(O)CH₂Cl, —OCH₂Ph, —O(CH₂)ⱼNH₂, —O(CH₂)ⱼN-phthalimide or a combination thereof;

R₂ is hydrogen, O-alkyl, O-haloalkyl, F, Cl, Br, I, haloalkyl, CF₃, CN, NO₂, —CH₂CN, NH₂, hydroxyl, COOH, C(O)H, NHCO-alkyl, —O(CH₂)ₖOCH₃, —O(CH₂)ₖOH, —O(CH₂)ₖNHCH₃, —O(CH₂)ₖNH₂, —O—(CH₂)ₖN(CH₃)₂, —OC(O)CF₃, —OC(O)CH₂Cl, —OCH₂Ph, —O(CH₂)ₖNH₂ or —O(CH₂)ₖN-phthalimide;

i, j, and k are independently an integer between 0 to 5;
n is an integer between 1 to 4;
or a metabolite, hydrate, isomer, N-oxide, prodrug, pharmaceutical product, pharmaceutically acceptable salt, polymorph, tautomer, or a combination thereof.

In one embodiment, this invention is directed to a compound of formula (III)

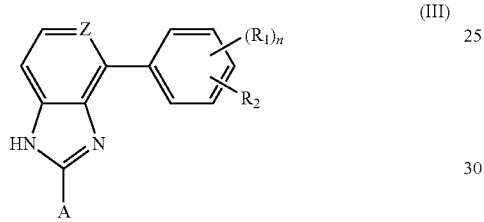

(III)

wherein

Z is CH or N;

A is substituted or unsubstituted phenyl; substituted or unsubstituted indolyl; or substituted or unsubstituted indazolyl;

wherein the optional substituents of A include O-alkyl, O-haloalkyl, F, Cl, Br, I, NO₂, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, —SO₂-aryl, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —C(O)NH₂ or a combination thereof;

R₁ is independently hydrogen, O-alkyl, O-haloalkyl, F, Cl, Br, I, haloalkyl, CF₃, CN, NO₂, —CH₂CN, NH₂, hydroxyl, COOH, C(O)H, NHCO-alkyl, —O(CH₂)ⱼOCH₃, —O(CH₂)ⱼOH, —O(CH₂)ⱼNHCH₃, —O(CH₂)ⱼNH₂, —O(CH₂)ⱼN(CH₃)₂, —OC(O)CF₃, —OC(O)CH₂Cl, —OCH₂Ph, —O(CH₂)ⱼNH₂, —O(CH₂)ⱼN-phthalimide or a combination thereof;

R₂ is hydrogen, O-alkyl, O-haloalkyl, F, Cl, Br, I, haloalkyl, CF₃, CN, NO₂, —CH₂CN, NH₂, hydroxyl, COOH, C(O)H, NHCO-alkyl, —O(CH₂)ₖOCH₃, —O(CH₂)ₖOH, —O(CH₂)ₖNHCH₃, —O(CH₂)ₖNH₂, —O(CH₂)ₖN(CH₃)₂, —OC(O)CF₃, —OC(O)CH₂Cl, —OCH₂Ph, —O(CH₂)ₖNH₂ or —O(CH₂)ₖN-phthalimide;

i, j, and k are independently an integer between 0 to 5;
n is an integer between 1 to 4;
or a metabolite, hydrate, isomer, N-oxide, prodrug, pharmaceutical product, pharmaceutically acceptable salt, polymorph, tautomer, or a combination thereof.

In one embodiment, this invention is directed to a compound of formula (IV)

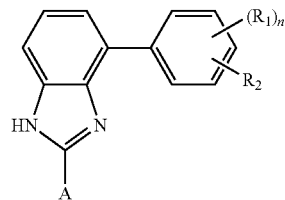

(IV)

wherein

A is substituted or unsubstituted phenyl; substituted or unsubstituted indolyl; or substituted or unsubstituted indazolyl;

wherein the optional substituents of A include O-alkyl, O-haloalkyl, F, Cl, Br, I, NO₂, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, —SO₂-aryl, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —C(O)NH₂ or a combination thereof;

R₁ is independently hydrogen, O-alkyl, O-haloalkyl, F, Cl, Br, I, haloalkyl, CF₃, CN, NO₂, —CH₂CN, NH₂, hydroxyl, COOH, C(O)H, NHCO-alkyl, —O(CH₂)ⱼOCH₃, —O(CH₂)ⱼOH, —O(CH₂)ⱼNHCH₃, —O(CH₂)ⱼNH₂, —O(CH₂)ⱼN(CH₃)₂, —OC(O)CF₃, —OC(O)CH₂Cl, —OCH₂Ph, —O(CH₂)ⱼNH₂, —O(CH₂)ⱼN-phthalimide or a combination thereof;

R₂ is hydrogen, O-alkyl, O-haloalkyl, F, Cl, Br, I, haloalkyl, CF₃, CN, NO₂, —CH₂CN, NH₂, hydroxyl, COOH, C(O)H, NHCO-alkyl, —O(CH₂)ₖOCH₃, —O(CH₂)ₖOH, —O(CH₂)ₖNHCH₃, —O(CH₂)ₖNH₂, —O(CH₂)ₖN(CH₃)₂, —OC(O)CF₃, —OC(O)CH₂Cl, —OCH₂Ph, —O(CH₂)ₖNH₂ or —O(CH₂)ₖN-phthalimide;

i, j, and k are independently an integer between 0 to 5;
n is an integer between 1 to 4;
or a metabolite, hydrate, isomer, N-oxide, prodrug, pharmaceutical product, pharmaceutically acceptable salt, polymorph, tautomer, or a combination thereof.

In one embodiment, this invention is directed to a compound of formula (V)

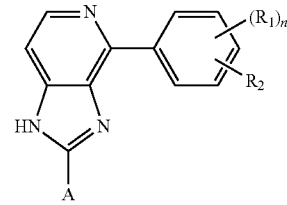

(V)

wherein

A is substituted or unsubstituted phenyl; substituted or unsubstituted indolyl; or substituted or unsubstituted indazolyl;

wherein the optional substituents of A include O-alkyl, O-haloalkyl, F, Cl, Br, I, NO₂, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, —SO₂-aryl, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —C(O)NH₂ or a combination thereof;

$R_1$ is independently hydrogen, O-alkyl, O-haloalkyl, F, Cl, Br, I, haloalkyl, $CF_3$, CN, $NO_2$, —$CH_2CN$, $NH_2$, hydroxyl, COOH, C(O)H, NHCO-alkyl, —$O(CH_2)_j$ $OCH_3$, —$O(CH_2)_jOH$, —$O(CH_2)_jNHCH_3$, —$O(CH_2)_j$ $NH_2$, —$O(CH_2)_jN(CH_3)_2$, —$OC(O)CF_3$, —$OC(O)$ $CH_2Cl$, —$OCH_2Ph$, —$O(CH_2)_jNH_2$, —$O(CH_2)_j$N-phthalimide or a combination thereof;

$R_2$ is hydrogen, O-alkyl, O-haloalkyl, F, Cl, Br, I, haloalkyl, $CF_3$, CN, $NO_2$, —$CH_2CN$, $NH_2$, hydroxyl, COOH, C(O)H, NHCO-alkyl, —$O(CH_2)_kOCH_3$, —$O(CH_2)_kOH$, —$O(CH_2)_kNHCH_3$, —$O(CH_2)_kNH_2$, —$O(CH_2)_kN(CH_3)_2$, —$OC(O)CF_3$, —$OC(O)CH_2Cl$, —$OCH_2Ph$, —$O(CH_2)_kNH_2$ or —$O(CH_2)_k$N-phthalimide;

i, j, and k are independently an integer between 0-5;

n is an integer between 1 to 4;

or a metabolite, hydrate, isomer, N-oxide, prodrug, pharmaceutical product, pharmaceutically acceptable salt, polymorph, tautomer, or a combination thereof.

In one embodiment, this invention is directed to a compound of formula (VI)

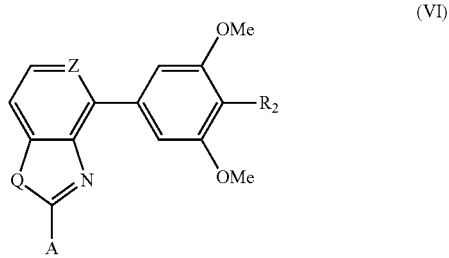

(VI)

wherein

Q is NH, S or O;

Z is CH or N;

A is substituted or unsubstituted phenyl; substituted or unsubstituted indolyl; or substituted or unsubstituted indazolyl;

wherein the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_i$ $NH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;

$R_2$ is hydrogen, O-alkyl, O-haloalkyl, F, Cl, Br, I, haloalkyl, $CF_3$, CN, $NO_2$, —$CH_2CN$, $NH_2$, hydroxyl, COOH, C(O)H, NHCO-alkyl, —$O(CH_2)_kOCH_3$, —$O(CH_2)_kOH$, —$O(CH_2)_kNHCH_3$, —$O(CH_2)_kNH_2$, —$O(CH_2)_kN(CH_3)_2$, —$OC(O)CF_3$, —$OC(O)CH_2Cl$, —$OCH_2Ph$, —$O(CH_2)_kNH_2$ or —$O(CH_2)_k$N-phthalimide;

i and k are independently an integer between 0 to 5;

or a metabolite, hydrate, isomer, N-oxide, prodrug, pharmaceutical product, pharmaceutically acceptable salt, polymorph, tautomer, or a combination thereof.

In one embodiment, this invention is directed to a compound of formula (VII)

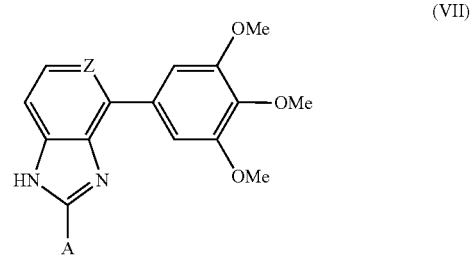

(VII)

wherein

Z is CH or N;

A is substituted or unsubstituted phenyl; substituted or unsubstituted indolyl; or substituted or unsubstituted indazolyl;

wherein the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_i$ $NH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;

i is an integer between 0 to 5;

or a metabolite, hydrate, isomer, N-oxide, prodrug, pharmaceutical product, pharmaceutically acceptable salt, polymorph, tautomer, or a combination thereof.

In one embodiment, this invention is directed to a compound of formula (VIII)

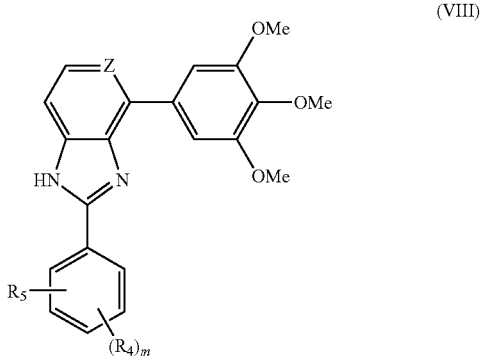

(VIII)

wherein

Z is CH or N;

$R_4$ is independently hydrogen, O-alkyl, O-haloalkyl, F, Cl, Br, I, $NO_2$, haloalkyl, $CF_3$, CN, —$CH_2CN$, $NH_2$, hydroxyl, —$(CH_2)_qNHCH_3$, —$(CH_2)_qNH_2$, —$(CH_2)_qN(CH_3)_2$, —$OC(O)CF_3$, —$SO_2$- aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;

$R_5$ is hydrogen, O-alkyl, O-haloalkyl, F, Cl, Br, I, $NO_2$, haloalkyl, $CF_3$, CN, —$CH_2CN$, $NH_2$, hydroxyl, —$(CH_2)_t$ $NHCH_3$, —$(CH_2)_tNH_2$, —$(CH_2)_tN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, or —$C(O)NH_2$;

m is an integer between 1 to 4;

t and q are independently integers between 0 to 5;

or a metabolite, hydrate, isomer, N-oxide, prodrug, pharmaceutical product, pharmaceutically acceptable salt, polymorph, tautomer, or a combination thereof.

In one embodiment, a compound of formula VIII is:

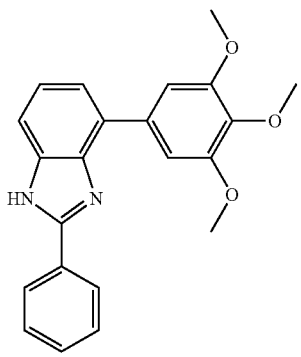

3 wherein its tautomer is:

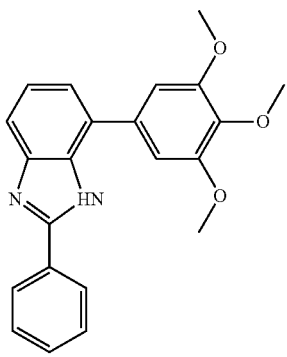 [SMILES: COc1cc(-c2cccc3nc(-c4ccccc4)[nH]c23)cc(OC)c1OC]

In one embodiment, this invention is directed to a compound of formula (IX)

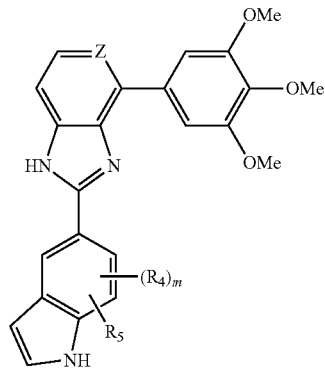

(IX)

wherein
Z is CH or N;
$R_4$ is independently hydrogen, O-alkyl, O-haloalkyl, F, Cl, Br, I, $NO_2$, haloalkyl, $CF_3$, CN, —$CH_2CN$, $NH_2$, hydroxyl, —$(CH_2)_qNHCH_3$, —$(CH_2)_qNH_2$, —$(CH_2)_qN(CH_3)_2$, —$OC(O)CF_3$, —$SO_2$- aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;
$R_5$ is hydrogen, O-alkyl, O-haloalkyl, F, Cl, Br, I, $NO_2$, haloalkyl, $CF_3$, CN, —$CH_2CN$, $NH_2$, hydroxyl, —$(CH_2)_tNHCH_3$, —$(CH_2)_tNH_2$, —$(CH_2)_tN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, or —$C(O)NH_2$;
m is an integer between 1 to 4;
t and q are independently integers between 0 to 5;
or a metabolite, hydrate, isomer, N-oxide, prodrug, pharmaceutical product, pharmaceutically acceptable salt, polymorph, tautomer, or a combination thereof In one embodiment, a compound of formula IX is:

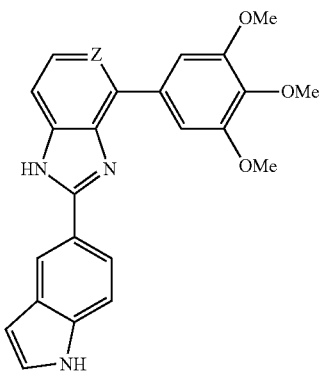

4 wherein its tautomer is:

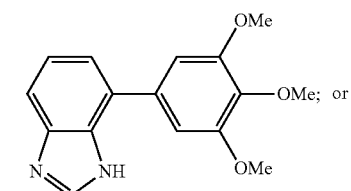

7

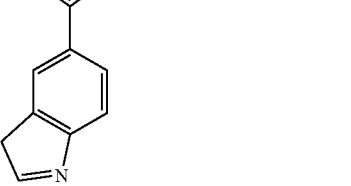

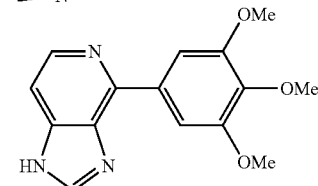

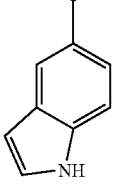

wherein its tautomer is:

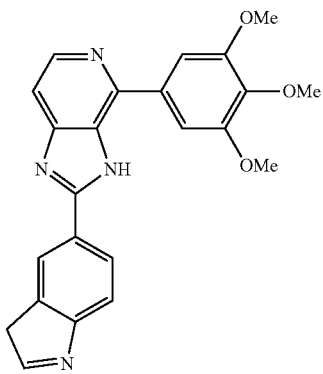 [SMILES: COc1cc(-c2nccc3nc(-c4ccc5c(c4)CC=N5)[nH]c23)cc(OC)c1OC]

In one embodiment, this invention is directed to a compound of formula (X)

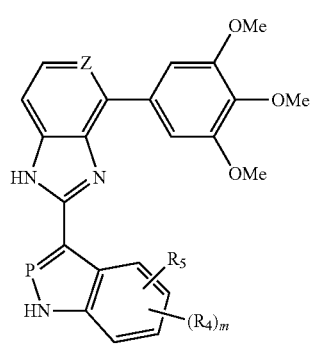

(X)

wherein

Z is CH or N;

P is CH or N;

R$_4$ is independently hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_q$NHCH$_3$, —(CH$_2$)$_q$NH$_2$, —(CH$_2$)$_q$N(CH$_3$)$_2$, —OC(O)CF$_3$, —SO$_2$- aryl, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or a combination thereof;

R$_5$ is hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_t$NHCH$_3$, —(CH$_2$)$_t$NH$_2$, —(CH$_2$)$_t$N(CH$_3$)$_2$, —OC(O)CF$_3$, —SO$_2$-aryl, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, or —C(O)NH$_2$;

m is an integer between 1 to 4;

t and q are independently integers between 0 to 5;

or a metabolite, hydrate, isomer, N-oxide, prodrug, pharmaceutical product, pharmaceutically acceptable salt, polymorph, tautomer, or a combination thereof.

In one embodiment, a compound of formula X is:

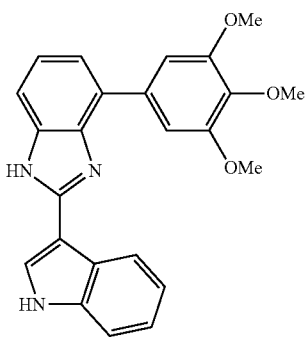

5 wherein its tautomer is:

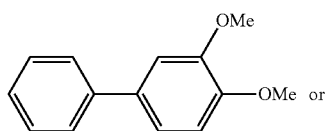

6

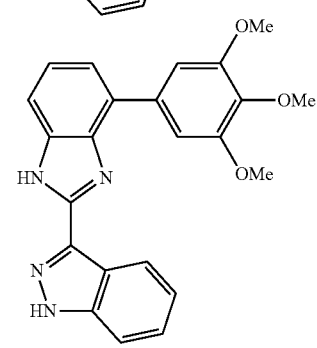

wherein its tautomer includes:

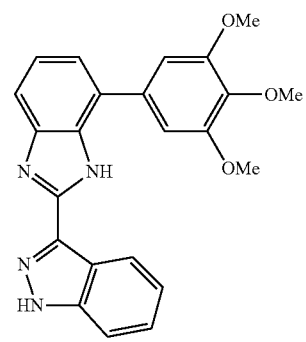 [SMILES: COc1cc(-c2cccc3nc(-c4n[nH]c5ccccc45)[nH]c23)cc(OC)c1OC]

In one embodiment, this invention is directed to a compound of formula (XI)

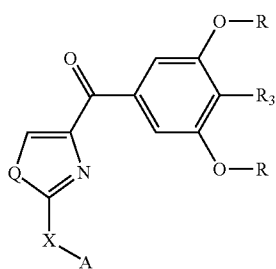

(XI)

wherein
Q is S, NH or O;
X is a bond or NH;
A is substituted or unsubstituted single-, fused- or multiple-ring aryl or (hetero)cyclic ring systems, including saturated and unsaturated N-heterocycles, saturated and unsaturated S-heterocycles, and saturated and unsaturated O-heterocycles, saturated or unsaturated cyclic hydrocarbons, saturated or unsaturated mixed heterocycles, aliphatic straight- or branched-chain $C_1$ to $C_{30}$ hydrocarbons; wherein the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;
R is hydrogen, $C_1$ to $C_5$ linear or branched alkyl; $C_1$ to $C_5$ linear or branched alkenyl, $(CH_2)_iPh$, aryl, $(CH_2)_iNHCH_3$, —$(CH_2)_iNH_2$, —$(CH_2)_iN(CH_3)_2$, C(O)alkyl, $C(O)CF_3$, —$(CH_2)_iOMe$, —$(CH_2)_iOH$ haloalkyl;
$R_3$ is hydrogen, O-alkyl, O-haloalkyl, F, Cl, Br, I, $NO_2$, haloalkyl, $CF_3$, CN, —$CH_2CN$, $NH_2$, hydroxyl, —$O(CH_2)_o$ $NHCH_3$, —$O(CH_2)_oNH_2$, —$O(CH_2)_oN(CH_3)_2$, —$O(CH_2)_o$ OMe, —$O(CH_2)_oOH$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, or —$C(O)NH_2$;
i, l, and o are independently an integer between 0 to 5;
or a metabolite, isomer, N-oxide, prodrug, hydrate, pharmaceutical product, pharmaceutically acceptable salt, polymorph, tautomer, or a combination thereof.

In one embodiment, this invention is directed to a compound of formula (XII)

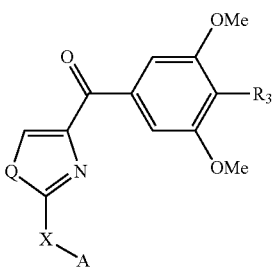

(XII)

wherein
Q is S, NH or O;
X is a bond or NH;
A is substituted or unsubstituted phenyl; substituted or unsubstituted indolyl; or substituted or unsubstituted indazolyl;

wherein the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_i$ $NH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO— alkyl, COOH, —C(O)Ph, C(O)O-alkyl, C(O)H, —$C(O)NH_2$ or a combination thereof;
$R_3$ is hydrogen, O-alkyl, O-haloalkyl, F, Cl, Br, I, $NO_2$, haloalkyl, $CF_3$, CN, —$CH_2CN$, $NH_2$, hydroxyl, —$O(CH_2)_o$ $NHCH_3$, —$O(CH_2)_oNH_2$, —$O(CH_2)_oN(CH_3)_2$, —$O(CH_2)_o$ OMe, —$O(CH_2)_oOH$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H or —$C(O)NH_2$;
i and o are independently an integer between 0 to 5;
or a metabolite, hydrate, isomer, N-oxide, prodrug, pharmaceutical product, pharmaceutically acceptable salt, polymorph, tautomer, or a combination thereof.

In one embodiment of formula XII, $R_3$ is different than OMe.

In one embodiment, this invention is directed to a compound of formula (XIII)

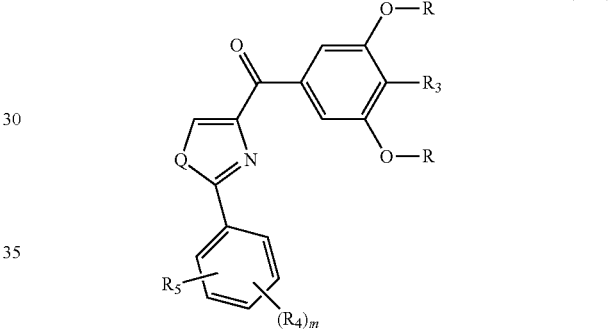

(XIII)

wherein
Q is S, NH or O;
R is hydrogen, $C_1$ to $C_5$ linear or branched alkyl; $C_1$ to $C_5$ linear or branched alkenyl, $(CH_2)_iPh$, aryl, $(CH_2)_iNHCH_3$, —$(CH_2)_iNH_2$, —$(CH_2)_iN(CH_3)_2$, C(O)alkyl, $C(O)CF_3$, —$(CH_2)_iOMe$, —$(CH_2)_iOH$ or haloalkyl;
$R_3$ is hydrogen, O-alkyl, O-haloalkyl, F, Cl, Br, I, $NO_2$, haloalkyl, $CF_3$, CN, —$CH_2CN$, $NH_2$, hydroxyl, —$O(CH_2)_o$ $NHCH_3$, —$O(CH_2)_oNH_2$, —$O(CH_2)_oN(CH_3)_2$, —$O(CH_2)_o$ OMe, —$O(CH_2)_oOH$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, or —$C(O)NH_2$;
$R_4$ is independently hydrogen, O-alkyl, O-haloalkyl, F, Cl, Br, I, $NO_2$, haloalkyl, $CF_3$, CN, —$CH_2CN$, $NH_2$, hydroxyl, —$(CH_2)_qNHCH_3$, —$(CH_2)_qNH_2$, —$(CH_2)_qN(CH_3)_2$, —OC$(O)CF_3$, —$SO_2$- aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or a combination thereof;
$R_5$ is hydrogen, O-alkyl, O-haloalkyl, F, Cl, Br, I, $NO_2$, haloalkyl, $CF_3$, CN, —$CH_2CN$, $NH_2$, hydroxyl, —$(CH_2)_t$ $NHCH_3$, —$(CH_2)_tNH_2$, —$(CH_2)_tN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, or —$C(O)NH_2$;
m is an integer between 1 to 4;
l, o, t and q are independently integers between 0 to 5;

or a metabolite, hydrate, isomer, N-oxide, prodrug, pharmaceutical product, pharmaceutically acceptable salt, polymorph, tautomer, or a combination thereof.

In one embodiment, a compound of formula XIII is:

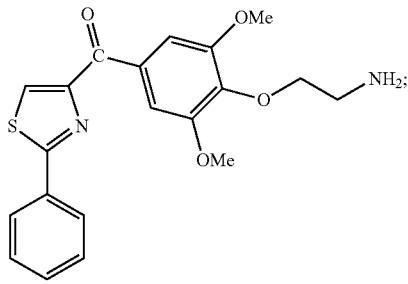

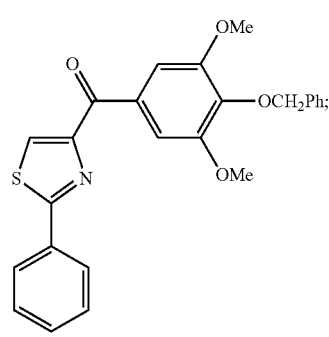

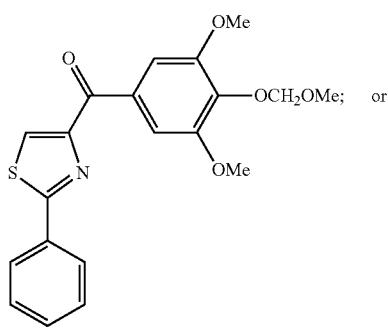

or

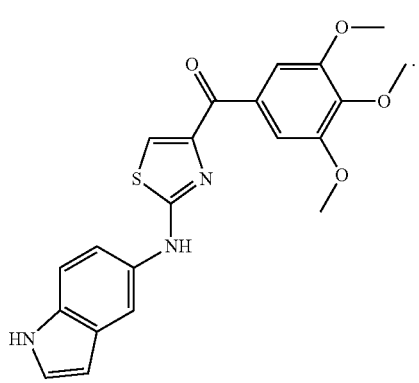

In one embodiment, this invention is directed to a compound of formula (XIV)

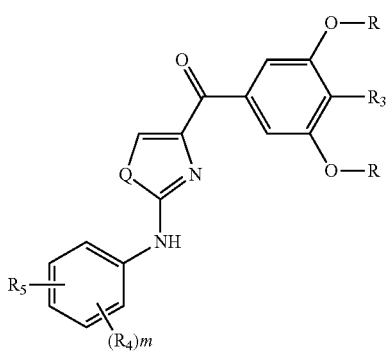

wherein
Q is S, NH or O;
R is hydrogen, $C_1$ to $C_5$ linear or branched alkyl, $C_1$ to $C_5$ linear or branched alkenyl, $(CH_2)_l$Ph, aryl, $(CH_2)_l$NHCH$_3$, —(CH$_2$)$_l$NH$_2$, —(CH$_2$)$_l$N(CH$_3$)$_2$, C(O)alkyl, C(O)CF$_3$, —(CH$_2$)$_l$OMe, —(CH$_2$)$_l$OH, or haloalkyl;
$R_3$ is hydrogen, O-alkyl, O-haloalkyl, F, Cl, Br, I, NO$_2$, haloalkyl, CF$_3$, CN, —CH$_2$CN, NH$_2$, hydroxyl, —O(CH$_2$)$_o$NHCH$_3$, —O(CH$_2$)$_o$NH$_2$, —O(CH$_2$)$_o$N(CH$_3$)$_2$, —O(CH$_2$)$_o$OMe, —O(CH$_2$)$_o$OH, —OC(O)CF$_3$, —SO$_2$-aryl, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H, or —C(O)NH$_2$;
$R_4$ is independently hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_q$NHCH$_3$, —(CH$_2$)$_q$NH$_2$, —(CH$_2$)$_q$N(CH$_3$)$_2$, —OC(O)CF$_3$, —SO$_2$- aryl, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or a combination thereof;
$R_5$ is hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_t$NHCH$_3$, —(CH$_2$)$_t$NH$_2$, —(CH$_2$)$_t$N(CH$_3$)$_2$, —OC(O)CF$_3$, —SO$_2$-aryl, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H, or —C(O)NH$_2$;
m is an integer between 1 to 4;
l, o, t and q are independently integers between 0 to 5;
or a metabolite, hydrate, pharmaceutical product, pharmaceutically acceptable salt, polymorph, tautomer, or a combination thereof.

In one embodiment, this invention is directed to a compound of formula (XV)

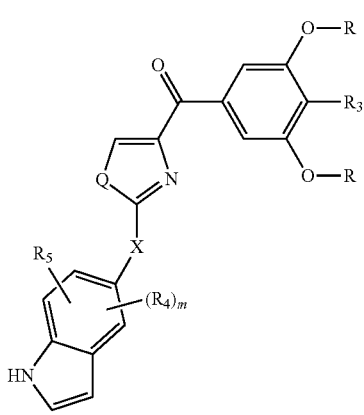

wherein

Q is S, NH or O;

X is a bond or NH;

R is hydrogen, $C_1$ to $C_5$ linear or branched alkyl, $C_1$ to $C_5$ linear or branched alkenyl, $(CH_2)_l$Ph, aryl, $(CH_2)_l$NHCH$_3$, —$(CH_2)_l$NH$_2$, —$(CH_2)_l$N(CH$_3$)$_2$, C(O)alkyl, C(O)CF$_3$, —$(CH_2)_l$OMe, —$(CH_2)_l$OH, or haloalkyl;

$R_3$ is hydrogen, O-alkyl, O-haloalkyl, F, Cl, Br, I, NO$_2$, haloalkyl, CF$_3$, CN, —CH$_2$CN, NH$_2$, hydroxyl, —O(CH$_2$)$_o$NHCH$_3$, —O(CH$_2$)$_o$NH$_2$, —O(CH$_2$)$_o$N(CH$_3$)$_2$, —O(CH$_2$)$_o$OMe, —O(CH$_2$)$_o$OH, —OC(O)CF$_3$, —SO$_2$-aryl, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H, or —C(O)NH$_2$;

$R_4$ is independently hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_q$NHCH$_3$, —(CH$_2$)$_q$NH$_2$, —(CH$_2$)$_q$N(CH$_3$)$_2$, —OC(O)CF$_3$, —SO$_2$- aryl, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$, or a combination thereof;

$R_5$ is hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_t$NHCH$_3$, —(CH$_2$)$_t$NH$_2$, —(CH$_2$)$_t$N(CH$_3$)$_2$, —OC(O)CF$_3$, —SO$_2$-aryl, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H or —C(O)NH$_2$;

m is an integer between 1 to 4;

l, o, t and q are independently integers between 0 to 5;

or a metabolite, hydrate, isomer, N-oxide, prodrug, pharmaceutical product, pharmaceutically acceptable salt, polymorph, tautomer, or a combination thereof.

In one embodiment of formula XI, XIII, XIV and XV, O—R is different than $R_3$.

Figure 3:
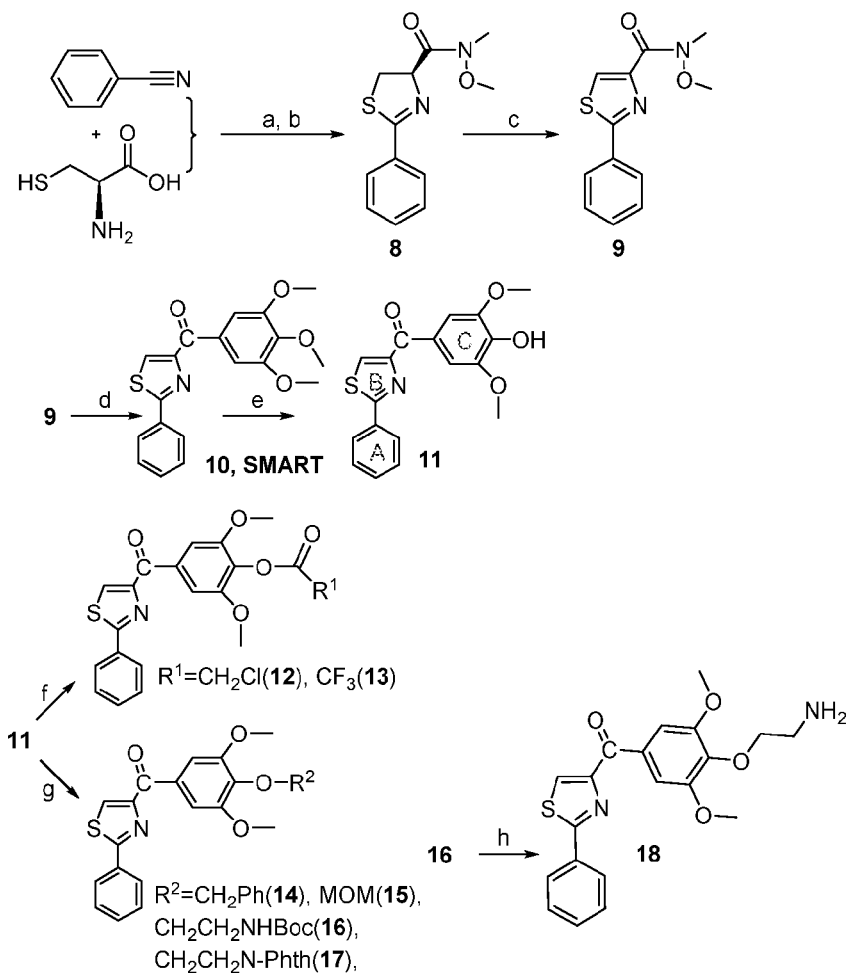
FIG. 3 depicts a synthetic scheme for the preparation of 4-substituted methoxybenzoyl-aryl-thiazole (SMART) analogues focused on modifications at para-position of the benzoyl ring. Reagents and conditions: (a) MeOH/pH=6.4 phosphate buffer, RT; (b) EDCI, HOBt, NMM, $CH_3OCH_3NH \cdot HCl$; (c) $CBrCl_3$, DBU; (d) 5-Bromo-1,2,3-trimethoxybenzene/BuLi, THF, $-78°$ C.; (e) $AlCl_3$, $CH_2Cl_2$; (f) $ClCH_2COCl$, $CH_2Cl_2$, $NEt_3$ (12) or $(CF_3CO)_2O$, $CH_2Cl_2$, DMAP (13); (g) $PhCH_2Br$, $K_2CO_3$, DMF (14); MOMCl, Hunig's base, $CH_2Cl_2$ (15); $BrCH_2CH_2NHBoc$, DMF, $Cs_2CO_3$ (16) or 2-(2-bromoethyl)isoindoline-1,3-dione, $K_2CO_3$, DMF $120°$ C. (17); (h) 4M HCl in dioxane.
Figure 5:
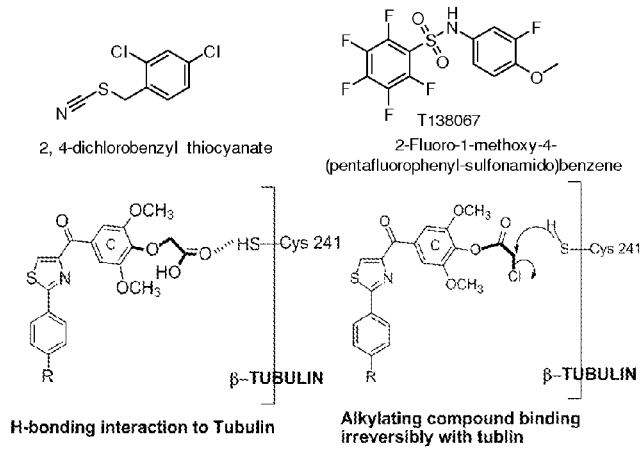
FIG. 5 depicts irreversible tubulin binding agents and hypothesis of interactions between Cys-241 and para-position at benzoyl ring of compounds of formula XI-XV.

In one embodiment, the compounds of formula XI-XV possess $R_3$ group at the para position of the benzoyl ring. It was found that introducing different functional groups at the para-position of benzoyl ring will likely form stronger interactions with Cys-241 in β-tubulin subunit (FIG. 5), and thus increasing the potency of inhibition of tubulin polymerization. Furthermore, the modification of the benzoyl ring resulted in better understanding of the potential metabolic demethylation mechanism. Both hydrophobic (OBn 14, OMOM 15) and hydrophilic (OCH$_2$CH$_2$NH$_2$, 18) groups were introduced, as shown in FIG. 3.

Another strategy came from the hypothesis that if an alkylating group was introduced at the para-position of the benzoyl ring, it may form an irreversible covalent bond with the mercapto group of Cys-241 in the colchicine binding domain and induce irreversible mitotic blocks. A well-described mechanism for inhibiting microtubule assembly is small molecule drugs binding to tubulin via covalent interaction with a tubulin amino residue. Bai et al. [Bai, R.; Covell, D. G.; Pei, X. F.; Ewell, J. B.; Nguyen, N. Y.; Brossi, A.; Hamel, E., Mapping the binding site of colchicinoids on beta-tubulin. 2-Chloroacetyl-2-demethylthiocolchicine covalently reacts predominantly with cysteine 239 and secondarily with cysteine 354. *J Biol Chem* 2000, 275(51), 40443-52.] reported that 2- and 3-chloroacetyl analogues of dimethylthiocolchicine bound irreversibly to the colchicine binding site primarily with Cys-241 and prevented colchicine binding agents from binding to the same site. The covalent interaction of 2,4-dichlorobenzyl thiocyanate (FIG. 5) with tubulin occurs at multiple cysteine residues, especially Cys-241 of β-tubulin [Bai, R. L.; Lin, C. M.; Nguyen, N. Y.; Liu, T. Y.; Hamel, E., Identification of the cysteine residue of beta-tubulin alkylated by the antimitotic agent 2,4-dichlorobenzyl thiocyanate, facilitated by separation of the protein subunits of tubulin by hydrophobic column chromatography. *Biochemistry* 1989, 28(13), 5606-12]. Formation of the covalent bond between tubulin and the 2,4-dichlorobenzyl mercaptan moiety appeared to be reversible. 2-Fluoro-1-methoxy-4-(pentafluorophenyl-sulfonamido) benzene (T138067, FIG. 5) irreversibly bound β-tubulin by the thiol group of Cys-241 displacing the para-F atom. It recruited unmodified tubulin dimers into large, amorphous aggregates, and thus quickly depleted the pool of tubulin available for microtubule formation [Shan, B.; Medina, J. C.; Santha, E.; Frankmoelle, W. P.; Chou, T. C.; Learned, R. M.; Narbut, M. R.; Stott, D.; Wu, P.; Jaen, J. C.; Rosen, T.; Timmermans, P. B.; Beckmann, H., Selective, covalent modification of beta-tubulin residue Cys-239 by T138067, an antitumor agent with in vivo efficacy against multidrug-resistant tumors. *Proceedings of the National Academy of Sciences of the United States of America* 1999, 96(10), 5686-91].

In one embodiment, the compounds of this invention introduce an alkylating functional group to form covalent bond or enhance the interaction between Cys-241 and the benzoyl ring of the compounds of this invention. Thus, chloroacetic analogue (12) and trifluoroacetate (13) in FIG. 3 were also synthesized and tested.

In one embodiment, A of formula I and XI is substituted or unsubstituted single-, fused- or multiple-ring aryl or (hetero)cyclic ring systems, including saturated and unsaturated N-heterocycles, saturated and unsaturated S-heterocycles, and saturated and unsaturated O-heterocycles, saturated or unsaturated cyclic hydrocarbons, saturated or unsaturated mixed heterocycles, aliphatic straight- or branched-chain $C_1$ to $C_{30}$ hydrocarbons.

In one embodiment, the A group is substituted or unsubstituted furanyl, benzofuranyl, benzothiophenyl, indolyl, indazolyl, pyridinyl, phenyl, biphenyl, triphenyl, diphenylmethane, adamantane-yl, fluorene-yl, or other heterocyclic analogs such as, e.g., pyrrolyl, pyrazolyl, imidazolyl, pyridinyl, pyrimidinyl, pyrazinyl, pyridazinyl, triazinyl, tetrazinyl, pyrrolizinyl, indolyl, isoquinolinyl, quinolinyl, benzimidazolyl, indazolyl, quinolizinyl, cinnolinyl, quinalolinyl, phthalazinyl, naphthyridinyl, quinoxalinyl, oxiranyl, oxetanyl, tetrahydrofuranyl, tetrahydropyranyl, dioxanyl, furanyl, pyrylium, benzodioxolyl, thiranyl, thietanyl, tetrahydrothiophene-yl, dithiolanyl, tetrahydrothiopyranyl, thiophene-yl, thiepinyl, thianaphthenyl, oxathiolanyl, morpholinyl, thioxanyl, thiazolyl, isothiazolyl, thiadiazolyl, oxazolyl, isoxazolyl, and oxadiazolyl.

As used herein, "saturated or unsaturated cyclic hydrocarbons" can be any such cyclic hydrocarbon, including but not limited to phenyl, biphenyl, triphenyl, naphthyl, cycloalkyl, cycloalkenyl, cyclodienyl, fluorene, adamantane, etc.; "saturated or unsaturated N-heterocycles" can be any such N-containing heterocycle, including but not limited to aza- and diaza-cycloalkyls such as aziridinyl, azetidinyl, diazatidinyl, pyrrolidinyl, piperidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, indazolyl, quinolinyl, isoquinolinyl, benzimidazolyl, indazolyl, quinolizinyl, cinnolinyl, quinalolinyl, phthalazinyl, naphthyridinyl, quinoxalinyl, etc.; "saturated or unsaturated O-heterocycles" can be any such O-containing heterocycle including but not limited to oxiranyl, oxetanyl, tetrahydrofuranyl, tetrahydropyranyl, dioxanyl, furanyl, pyrylium, benzofuranyl, benzodioxolyl, etc.; "saturated or unsaturated S-heterocycles" can be any such S-containing heterocycle, including but not limited to thiranyl, thietanyl, tetrahydrothiophene-yl, dithiolanyl, tetrahydrothiopyranyl, thiophene-yl, thiepinyl, thianaphthenyl, etc.; "saturated or unsaturated mixed heterocycles" can be any heterocycle containing two or more S-, N-, or O-heteroatoms, including but not limited to oxathiolanyl, morpholinyl, thioxanyl, thiazolyl, isothiazolyl, thiadiazolyl, oxazolyl, isoxazolyl, oxadiaziolyl, etc.

In one embodiment, A of formula II-VII and XII is substituted or unsubstituted phenyl; substituted or unsubstituted indolyl; or substituted or unsubstituted indazolyl. In another embodiment, A of formula I, II-VII, XI and XII is substituted or unsubstituted phenyl. In another embodiment, A of formula I, II-VII, XI and XII is substituted or unsubstituted indolyl. In another embodiment, the indolyl is substituted or unsubstituted 3-indolyl, 4-indolyl or 5-indolyl. In another embodiment, the A group is substituted or unsubstituted 3-indolyl. In certain embodiments, the A group is unsubstituted 3-indolyl. In certain embodiments, the A group is unsubstituted 5-indolyl. In certain embodiments, the A group is substituted 5-indolyl. In another embodiment, the indolyl is substituted or unsubstituted selected from the following structures:

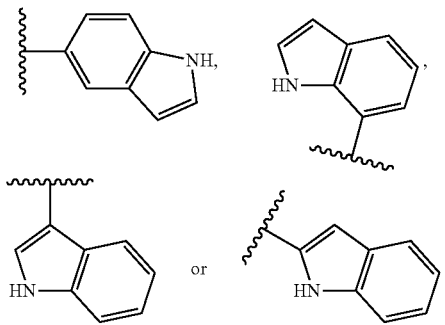

In another embodiment, A of formula I, II-VII, XI and XII is substituted or unsubstituted indazolyl. In another embodiment, the indazolyl is substituted or unsubstituted 3-indazolyl, 4-indazolyl or 5-indazolyl. In another embodiment, the A group is substituted or unsubstituted 3-indazolyl. In certain embodiments, the A group is unsubstituted 3-indazolyl. In certain embodiments, the A group is unsubstituted 5-indazolyl. In certain embodiments, the A group is substituted 5-indazolyl. In another embodiment, the indazolyl is substituted or unsubstituted selected from the following structures:

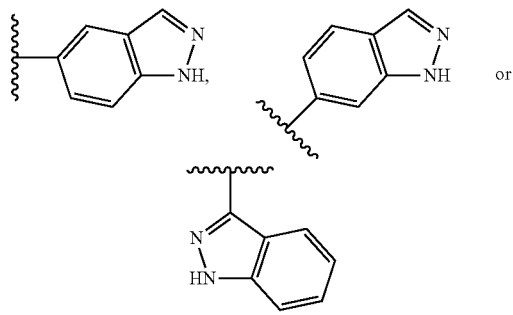

In one embodiment, the optional substituents of A of formula I, II-VII, XI and XII include unsubstituted, or one, two, three, four or five substituents. In another embodiment, the substituents are the same. In another embodiment, the substituents are different. Single substituents can be present at the ortho, meta, or para positions. In some embodiments, when two or more substituents are present, one of them is at the para position.

In another embodiments, the optional substituents of A include O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$, $NO_2$ or a combination thereof. In another embodiment, A is unsubstituted. In another embodiment, A is substituted by O-alkyl. In another embodiment, A is substituted by O-haloalkyl. In another embodiment, A is substituted by halogen. In another embodiment, A is substituted by $NO_2$. In another embodiment, A is substituted by haloalkyl. In another embodiment, A is substituted by $CF_3$. In another embodiment, A is substituted by CN. In another embodiment, A is substituted by —$CH_2CN$. In another embodiment, A is substituted by $NH_2$. In another embodiment, A is substituted by hydroxyl. In another embodiment, A is substituted by —$(CH_2)_iNHCH_3$. In another embodiment, A is substituted by —$(CH_2)_iNH_2$. In another embodiment, A is substituted by —$(CH_2)_iN(CH_3)_2$. In another embodiment, A is substituted by —$OC(O)CF_3$. In another embodiment, A is substituted by —$SO_2$-aryl. In another embodiment, A is substituted by $C_1$-$C_5$ linear or branched alkyl. In another embodiment, A is substituted by haloalkyl. In another embodiment, A is substituted by alkylamino. In another embodiment, A is substituted by aminoalkyl. In another embodiment, A is substituted by —$OCH_2Ph$. In another embodiment, A is substituted by —NHCO-alkyl. In another embodiment, A is substituted by COOH. In another embodiment, A is substituted by —C(O)Ph. In another embodiment, A is substituted by C(O)O-alkyl. In another embodiment, A is substituted by C(O)H. In another embodiment, A is substituted by —$C(O)NH_2$.

In one embodiment, i is an integer between 0 to 5. In another embodiment, i is 0. In another embodiment, i is 1. In another embodiment, i is 2. In another embodiment, i is 3. In another embodiment, i is 4. In another embodiment, i is 5.

In one embodiment, Z of formula I-III and VI-X is CH or N. In another embodiment Z is CH. In another embodiment, Z is N.

In one embodiment, P of formula X is CH or N. In another embodiment P is CH. In another embodiment, P is N.

In one embodiment, Q of formula I, II, VI, XI, XII and XIII is S, O or NH. In another embodiment Q is S. In another embodiment, Q is O. In another embodiment Q is NH.

In one embodiment, X of formula XI and XV is a bond or NH. In another embodiment, X is a bond. In another embodiment, X is NH.

In one embodiment, $R_1$ of formula I-V is hydrogen, O-alkyl, O-haloalkyl, F, Cl, Br, I, haloalkyl, $CF_3$, CN, $NO_2$, —$CH_2CN$, $NH_2$, hydroxyl, COOH, C(O)H, NHCO-alkyl, —$O(CH_2)_jOCH_3$, —$O(CH_2)_jOH$, —$O(CH_2)_jNHCH_3$, —$O(CH_2)_jNH_2$, —O—$(CH_2)_jN(CH_3)_2$, —$OC(O)CF_3$, —$OC(O)CH_2Cl$, —$OCH_2Ph$, —$O(CH_2)_jNH_2$ or —$O(CH_2)_j$N-phthalimide. In another embodiment, $R_1$ is hydrogen. In another embodiment, $R_1$ is O-alkyl. In another embodiment, $R_1$ is O-haloalkyl. In another embodiment, $R_1$ is halogen. In another embodiment, $R_1$ is haloalkyl. In another embodiment, $R_1$ is $CF_3$. In another embodiment, $R_1$ is CN. In another embodiment, $R_1$ is $NO_2$. In another embodiment, $R_1$ is —$CH_2CN$. In another embodiment, $R_1$ is $NH_2$. In another embodiment, $R_1$ is hydroxyl. In another embodiment, $R_1$ is COOH. In another embodiment, $R_1$ is C(O)H. In another embodiment, $R_1$ is NHCO-alkyl. In another embodiment, $R_1$ is —O(CH$_2$)$_j$OCH$_3$. In another embodiment, $R_1$ is —O(CH$_2$)$_j$OH. In another embodiment, $R_1$ is —O(CH$_2$)$_j$NHCH$_3$. In another embodiment, $R_1$ is —O(CH$_2$)$_j$NH$_2$. In another embodiment, $R_1$ is —O—(CH$_2$)$_j$N(CH$_3$)$_2$. In another embodiment, $R_1$ is —OC(O)CF$_3$. In another embodiment, $R_1$ is —OC(O)CH$_2$Cl. In another embodiment, $R_1$ is —OCH$_2$Ph. In another embodiment, $R_1$ is —O(CH$_2$)$_j$NH$_2$. In another embodiment, $R_1$ is or —O(CH$_2$)$_j$N-phthalimide.

In one embodiment, j is an integer between 0 to 5. In another embodiment, j is 0. In another embodiment, j is 1. In another embodiment, j is 2. In another embodiment, j is 3. In another embodiment, j is 4. In another embodiment, j is 5.

In one embodiment, n is an integer between 1 to 4. In another embodiment, n is 1. In another embodiment, n is 2, in another embodiment, n is 3. In another embodiment, n is 4.

In one embodiment, $R_2$ of formula I-VI is hydrogen, O-alkyl, O-haloalkyl, F, Cl, Br, I, haloalkyl, CF$_3$, CN, NO$_2$, —CH$_2$CN, NH$_2$, hydroxyl, COOH, C(O)H, NHCO-alkyl, —O(CH$_2$)$_j$OCH$_3$, —O(CH$_2$)$_j$OH, —O(CH$_2$)$_j$NHCH$_3$, —O(CH$_2$)$_j$NH$_2$, —O—(CH$_2$)$_j$N(CH$_3$)$_2$, —OC(O)CF$_3$, —OC(O)CH$_2$Cl, —OCH$_2$Ph, —O(CH$_2$)$_j$NH$_2$ or —O(CH$_2$)$_j$N-phthalimide. In another embodiment, $R_2$ is hydrogen. In another embodiment, $R_2$ is O-alkyl. In another embodiment, $R_2$ is O-haloalkyl. In another embodiment, $R_2$ is halogen. In another embodiment, $R_2$ is haloalkyl. In another embodiment, $R_2$ is CF$_3$. In another embodiment, $R_2$ is CN. In another embodiment, $R_2$ is NO$_2$. In another embodiment, $R_2$ is —CH$_2$CN. In another embodiment, $R_2$ is NH$_2$. In another embodiment, $R_2$ is hydroxyl. In another embodiment, $R_1$ is COOH. In another embodiment, $R_2$ is C(O)H. In another embodiment, $R_2$ is NHCO-alkyl. In another embodiment, $R_2$ is —O(CH$_2$)$_k$OCH$_3$. In another embodiment, $R_2$ is —O(CH$_2$)$_k$OH. In another embodiment, $R_2$ is —O(CH$_2$)$_k$NHCH$_3$. In another embodiment, $R_2$ is —O(CH$_2$)$_k$NH$_2$. In another embodiment, $R_2$ is —O—(CH$_2$)$_k$N(CH$_3$)$_2$. In another embodiment, $R_2$ is —OC(O)CF$_3$. In another embodiment, $R_2$ is —OC(O)CH$_2$Cl. In another embodiment, $R_2$ is —OCH$_2$Ph. In another embodiment, $R_2$ is —O(CH$_2$)$_k$NH$_2$. In another embodiment, $R_2$ is or —O(CH$_2$)$_k$N-phthalimide.

In one embodiment, at least one of $R_1$ and $R_2$ of formula I-V is not hydrogen.

In one embodiment, k is an integer between 0 to 5. In another embodiment, k is 0. In another embodiment, k is 1. In another embodiment, k is 2. In another embodiment, k is 3. In another embodiment, k is 4. In another embodiment, k is 5.

In one embodiment, $R_3$ of formula XI-XV is hydrogen, O-alkyl, O-haloalkyl, F, Cl, Br, I, NO$_2$, haloalkyl, CF$_3$, CN, —CH$_2$CN, NH$_2$, hydroxyl, —O(CH$_2$)$_o$NHCH$_3$, —O(CH$_2$)$_o$NH$_2$, —O(CH$_2$)$_o$N(CH$_3$)$_2$, —O(CH$_2$)$_o$OMe, —O(CH$_2$)$_o$OH, —OC(O)CF$_3$, —SO$_2$-aryl, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, or —C(O)NH$_2$. In another embodiment, $R_3$ is hydrogen. In another embodiment, $R_3$ is O-alkyl. In another embodiment, $R_3$ is O-haloalkyl. In another embodiment, $R_3$ is halogen. In another embodiment, $R_3$ is NO$_2$. In another embodiment, $R_3$ is haloalkyl. In another embodiment, $R_3$ is CF$_3$. In another embodiment, $R_3$ is CN. In another embodiment, $R_3$ is —CH$_2$CN. In another embodiment, $R_3$ is NH$_2$. In another embodiment, $R_3$ is hydroxyl. In another embodiment, $R_3$ is —O(CH$_2$)$_o$NHCH$_3$. In another embodiment, $R_3$ is —O(CH$_2$)$_o$NH$_2$. In another embodiment, $R_3$ is —O(CH$_2$)$_o$N(CH$_3$)$_2$. In another embodiment, $R_3$ is —O(CH$_2$)$_o$OMe. In another embodiment, $R_3$ is —O(CH$_2$)$_o$OH. In another embodiment, $R_3$ is —OC(O)CF$_3$. In another embodiment, $R_3$ is —SO$_2$-aryl. In another embodiment, $R_3$ is C$_1$-C$_5$ linear or branched alkyl. In another embodiment, $R_3$ is haloalkyl. In another embodiment, $R_3$ is alkylamino. In another embodiment, $R_3$ is aminoalkyl. In another embodiment, $R_3$ is —OCH$_2$Ph. In another embodiment, $R_3$ is —NHCO-alkyl. In another embodiment, $R_3$ is COOH. In another embodiment, $R_3$ is —C(O)Ph. In another embodiment, $R_3$ is C(O)O-alkyl. In another embodiment, $R_3$ is C(O)H. In another embodiment, $R_3$ is —C(O)NH$_2$.

In one embodiment, o is an integer between 0 to 5. In another embodiment, o is 0. In another embodiment, o is 1. In another embodiment, o is 2. In another embodiment, o is 3. In another embodiment, o is 4. In another embodiment, o is 5. In one embodiment $R_4$ of formula VIII-X and XIII-XV is independently hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_q$NHCH$_3$, —(CH$_2$)$_q$NH$_2$, —(CH$_2$)$_q$N(CH$_3$)$_2$, —OC(O)CF$_3$, —SO$_2$-aryl, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or a combination thereof. In another embodiment, $R_4$ is hydrogen. In another embodiment, $R_4$ is O-alkyl. In another embodiment, $R_4$ is O-haloalkyl. In another embodiment, $R_4$ is halogen. In another embodiment, $R_4$ is NO$_2$. In another embodiment, $R_4$ is haloalkyl. In another embodiment, $R_4$ is CF$_3$. In another embodiment, $R_4$ is CN. In another embodiment, $R_4$ is —CH$_2$CN. In another embodiment, $R_4$ is NH$_2$. In another embodiment, $R_4$ is hydroxyl. In another embodiment, $R_4$ is —(CH$_2$)$_q$NHCH$_3$. In another embodiment, $R_4$ is —(CH$_2$)$_q$NH$_2$. In another embodiment, $R_4$ is —(CH$_2$)$_q$N(CH$_3$)$_2$. In another embodiment, $R_4$ is —OC(O)CF$_3$. In another embodiment, $R_4$ is —SO$_2$-aryl. In another embodiment, $R_4$ is C$_1$-C$_5$ linear or branched alkyl. In another embodiment, $R_4$ is haloalkyl. In another embodiment, $R_4$ is alkylamino. In another embodiment, $R_4$ is aminoalkyl. In another embodiment, $R_4$ is —OCH$_2$Ph. In another embodiment, $R_4$ is —NHCO-alkyl. In another embodiment, $R_4$ is COOH. In another embodiment, $R_4$ is —C(O)Ph. In another embodiment, $R_4$ is C(O)O-alkyl. In another embodiment, $R_4$ is C(O)H. In another embodiment, $R_4$ is —C(O)NH$_2$.

In one embodiment, q is an integer between 0 to 5. In another embodiment, q is 0. In another embodiment, q is 1. In another embodiment, q is 2. In another embodiment, q is 3. In another embodiment, q is 4. In another embodiment, q is 5. In one embodiment, m is an integer between 1 to 4. In another embodiment, m is 1. In another embodiment, m is 2. In another embodiment, m is 3. In another embodiment, m is 4.

In one embodiment $R_5$ of formula VIII-X and XIII-XV is hydrogen, O-alkyl, O-haloalkyl, F, Cl, Br, I, NO$_2$, haloalkyl, CF$_3$, CN, —CH$_2$CN, NH$_2$, hydroxyl, —(CH$_2$)$_q$NHCH$_3$, —(CH$_2$)$_q$NH$_2$, —(CH$_2$)$_q$N(CH$_3$)$_2$, —OC(O)CF$_3$, —SO$_2$-aryl, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, or —C(O)NH$_2$. In another embodiment, $R_5$ is hydrogen. In another embodiment, $R_5$ is O-alkyl. In another embodiment, $R_5$ is O-haloalkyl. In another embodiment, $R_5$ is halogen. In another embodiment, $R_5$ is NO$_2$. In another embodiment, $R_5$ is haloalkyl. In another embodiment, $R_5$ is CF$_3$. In another embodiment, $R_5$ is CN. In another embodiment, $R_5$ is —CH$_2$CN. In another embodiment, $R_5$ is $NH_2$. In another embodiment, $R_5$ is hydroxyl. In another embodiment, $R_5$ is —$(CH_2)_tNHCH_3$. In another embodiment, $R_5$ is —$(CH_2)_tNH_2$. In another embodiment, $R_5$ is —$(CH_2)_tN(CH_3)_2$. In another embodiment, $R_5$ is —$OC(O)CF_3$. In another embodiment, $R_5$ is —$SO_2$-aryl. In another embodiment, $R_5$ is $C_1$-$C_5$ linear or branched alkyl. In another embodiment, $R_5$ is haloalkyl. In another embodiment, $R_5$ is alkylamino. In another embodiment, $R_5$ is aminoalkyl. In another embodiment, $R_5$ is —$OCH_2Ph$. In another embodiment, $R_5$ is —NHCO-alkyl. In another embodiment, $R_5$ is COOH. In another embodiment, $R_5$ is —C(O)Ph. In another embodiment, $R_5$ is C(O)O-alkyl. In another embodiment, $R_5$ is C(O)H. In another embodiment, $R_5$ is —$C(O)NH_2$.

In one embodiment, t is an integer between 0 to 5. In another embodiment, t is 0. In another embodiment, t is 1. In another embodiment, t is 2. In another embodiment, t is 3. In another embodiment, t is 4. In another embodiment, t is 5.

In one embodiment, R of formula XI, XIII-XV is R is hydrogen, $C_1$ to $C_5$ linear or branched alkyl; $C_1$ to $C_5$ linear or branched alkenyl, $(CH_2)_lPh$, aryl, $(CH_2)_lNHCH_3$, —$(CH_2)_lNH_2$, —$(CH_2)_lN(CH_3)_2$, C(O)alkyl, $C(O)CF_3$, —$(CH_2)_lOMe$, —$(CH_2)_lOH$, or haloalkyl. In another embodiment, R is hydrogen. In another embodiment, R is $C_1$ to $C_5$ linear or branched alkyl. In another embodiment, R is $C_1$ to $C_5$ linear or branched alkenyl. In another embodiment, R is $(CH_2)_lPhe$. In another embodiment, R is aryl. In another embodiment, R is $(CH_2)_lNHCH_3$. In another embodiment, R is —$(CH_2)_lNH_2$. In another embodiment, R is —$(CH_2)_lN(CH_3)_2$. In another embodiment, R is C(O)alkyl. In another embodiment, R is $C(O)CF_3$. In another embodiment, R is —$(CH_2)_lOMe$. In another embodiment, R is —$(CH_2)_lOH$. In another embodiment, R is haloalkyl.

In one embodiment, l is an integer between 0 to 5. In another embodiment, l is 0. In another embodiment, l is 1. In another embodiment, l is 2. In another embodiment, l is 3. In another embodiment, l is 4. In another embodiment, l is 5.

As used herein, the term "alkyl" can be any straight- or branched-chain alkyl group containing up to about 30 carbons unless otherwise specified. In another embodiment, the alkyl is a $C_1$-$C_5$ alkyl. In another embodiment, the alkyl is a $C_2$-$C_5$ alkyl. In another embodiment, the alkyl is a $C_1$-$C_7$ alkyl. The alkyl group can be a sole substituent or it can be a component of a larger substituent, such as in an alkoxy, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, etc.

As used herein, the term "aryl" refers to any aromatic ring substituent that is directly bonded to the $R^1$ or $R^2$ ring member(s). The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are —$N(Me)_2$, —NHMe, —$NH_3$.

A "haloalkyl" group refers, in another embodiment, to an alkyl group as defined above, which is substituted by one or more halogen atoms, e.g. by F, Cl, Br or I. Nonlimiting examples of haloalkyl groups are $CF_3$, $CF_2CF_3$, $CH_2CF_3$.

In one embodiment, this invention provides a compound of this invention or its metabolite, pharmaceutically acceptable salt, pharmaceutical product, hydrate, isomer, N-oxide, prodrug, tautomer, polymorph, or combinations thereof. In one embodiment, this invention provides a metabolite of the compound of this invention. In another embodiment, this invention provides a pharmaceutically acceptable salt of the compound of this invention. In another embodiment, this invention provides a pharmaceutical product of the compound of this invention. In another embodiment, this invention provides a hydrate of the compound of this invention. In another embodiment, this invention provides an isomer of the compound of this invention. In another embodiment, this invention provides N-oxide of the compound of this invention. In another embodiment, this invention provides a prodrug of the compound of this invention. In another embodiment, this invention provides a tautomer of the compound of this invention. In another embodiment, this invention provides a polymorph of the compound of this invention. In another embodiment, this invention provides composition comprising a compound of this invention, as described herein, or, in another embodiment, a combination of a metabolite, pharmaceutically acceptable salt, pharmaceutical product, hydrate, isomer, N-oxide, prodrug or polymorph of the compound of this invention.

Compounds of the present invention can also be in the form of a hydrate, which means that the compound further includes a stoichiometric or non-stoichiometric amount of water bound by non-covalent intermolecular forces.

Compounds of the present invention may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example the following tautomers, but not limited to these, are included.

Tautomerization of the Imidazole Ring

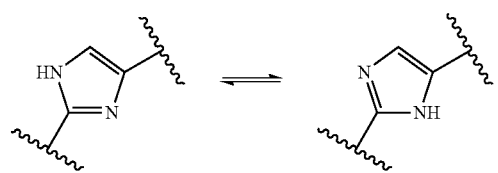 [SMILES: *c1c[nH]c(*)n1 ; *c1cnc(*)[nH]1]

Tautomers of the Indazole Ring

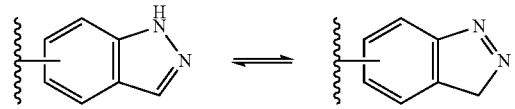

Tautomers of the Benzimidazole Ring

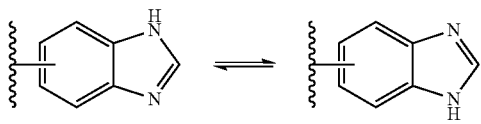

Tautomers of the Pyridino-Imidazole Ring

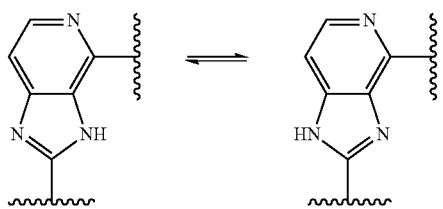 [SMILES: *c1nc2ccnc(*)c2[nH]1 ; *c1nc2c(*)nccc2[nH]1]

The tautomers of this invention are freely interconverting tautomers, not unresolved mixtures. The imidazoles, thiazole and other ring systems of this invention are tautomerizable. All tautomers are considered as part of the invention.

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of the compounds of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the term "isomer" includes, but is not limited to, optical isomers and analogs, structural isomers and analogs, conformational isomers and analogs, and the like.

In one embodiment, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the invention provides a compound of this invention or an N-oxide thereof.

The compounds of the present invention may also be administered as metabolites. In one embodiment, the term "metabolite" refers to any substance produced from another substance by metabolism or a metabolic process. In another embodiment, the metabolites of this invention include M1 to M14 as described in Example 6 and FIGS. 8-11.

Thus, certain derivatives which may have little or no pharmacological activity themselves can, when administered into or onto the body, be converted into compounds of the present invention having the desired activity, for example, by hydrolytic cleavage. Further information on the use of prodrugs may be found in *Pro-drugs as Novel Delivery Systems*, Vol. 14, ACS Symposium Series (Higuchi and Stella); and *Bioreversible Carriers in Drug Design*, Pergamon Press (ed. E B Roche, American Pharmaceutical Association) (1987), each of which is hereby incorporated by reference in its entirety.

Prodrugs can, for example, be produced by replacing appropriate functionalities present in the compounds of the present invention with certain moieties known to those skilled in the art as pro-moieties. Examples of such prodrugs include, without limitation, replacement of hydrogen in an alcohol functionality (—OH) by a C1 to C6 alkyl to form an ether; and (ii) replacement of hydrogen in a secondary amino functionality with a C1 to C10 alkanoyl to form an amide.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In one embodiment, the compounds of this invention are administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a compound of this invention as described hereinabove.

Yet another aspect of the present invention relates to a method of treating cancer that includes selecting a subject in need of treatment for cancer, and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

The compounds of the present invention are useful in the treatment or prevention of various forms of cancer, particularly prostate cancer, breast cancer, drug-resistant breast cancer, ovarian, skin cancer (e.g., melanoma), drug-resistant melanoma, lung cancer, colon cancer, leukemia, renal cancer, CNS cancer (e.g., glioma, glioblastoma). Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

Thus, a further aspect of the present invention relates to a method of destroying a cancerous cell that includes: providing a compound of the present invention and then contacting a cancerous cell with the compound under conditions effective to destroy the contacted cancerous cell. According to various embodiments of destroying the cancerous cells, the cells to be destroyed can be located either in vivo or ex vivo (i.e., in culture).

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

When the compounds or pharmaceutical compositions of the present invention are administered to treat or prevent a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In one embodiment, this invention is directed to a method of treating, suppressing, reducing the severity, reducing the risk of developing or inhibiting cancer comprising administering a compound of this invention to a subject suffering from cancer under conditions effective to treat the cancer.

Drug resistance is the major cause of cancer chemotherapy failure. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism.

In one embodiment, this invention provides methods for: a) treating, suppressing, reducing the severity, reducing the risk, or inhibiting cancer; b) treating, suppressing, reducing the severity, reducing the risk, or inhibiting prostate cancer; c) treating, suppressing, reducing the severity, reducing the risk, or inhibiting drug-resistant prostate cancer; d) treating, suppressing, reducing the severity, reducing the risk, or inhibiting breast cancer; e) treating, suppressing, reducing the severity, reducing the risk, or inhibiting drug-resistant breast cancer; f) treating, suppressing, reducing the severity, reducing the risk, or inhibiting ovarian cancer; g) treating, suppressing, reducing the severity, reducing the risk, or inhibiting drug-resistant ovarian cancer; h) treating, suppressing, reducing the severity, reducing the risk, or inhibiting skin cancer; i) treating, suppressing, reducing the severity, reducing the risk, or inhibiting melanoma; j) treating, suppressing, reducing the severity, reducing the risk, or inhibiting metastatic melanoma; k) treating, suppressing, reducing the severity, reducing the risk, or inhibiting drug-resistant melanoma; l) treating, suppressing, reducing the severity, reducing the risk, or inhibiting lung cancer; m) treating, suppressing, reducing the severity, reducing the risk, or inhibiting colon cancer; n) treating, suppressing, reducing the severity, reducing the risk, or inhibiting glioma; o) treating, suppressing, reducing the severity, reducing the risk, or inhibiting leukemia; p) treating, suppressing, reducing the severity, reducing the risk, or inhibiting lymphoma; q) treating, suppressing, reducing the severity, reducing the risk, or inhibiting renal cancer; r) treating, suppressing, reducing the severity, reducing the risk, or inhibiting CNS cancer; s) treating, suppressing, reducing the severity, reducing the risk, or inhibiting uterine cancer; t) treating, suppressing, reducing the severity, reducing the risk, or inhibiting drug-resistant uterine cancer; u) treating a drug resistant tumor or tumors wherein said tumor is selected from the group consisting of prostate cancer tumor, drug-resistant prostate cancer tumor, breast cancer tumor, drug-resistant breast cancer tumor, glioma tumor, ovarian cancer tumor, drug-resistant ovarian cancer tumor, skin cancer tumor, melanoma tumor, drug-resistant melanoma tumor, lung cancer tumor, colon cancer tumor, leukemia tumor, lymphoma tumor, renal cancer tumor, CNS cancer tumor, uterine cancer tumor, drug-resistant uterine cancer tumor, and combinations thereof; comprising administering a compound of this invention and/or a metabolite, pharmaceutically acceptable salt, pharmaceutical product, tautomer, hydrate, isomer, N-oxide, prodrug, polymorph, of said compound, or any combination thereof. In another embodiment, the subject has been previously treated with chemotherapy, radiotherapy, or biological therapy.

The compounds of the present invention are useful in the treatment, reducing the severity, reducing the risk, or inhibition of cancer, metastatic cancer, drug resistant tumors, drug resistant cancer and various forms of cancer. In a preferred embodiment the cancer is prostate cancer, drug-resistant prostate cancer, breast cancer, drug-resistant breast cancer, ovarian cancer, drug-resistant ovarian cancer, uterine cancer, drug-resistant uterine cancer, skin cancer (e.g., melanoma), drug-resistant melanoma, lung cancer, colon cancer, leukemia, lymphoma, head and neck, pancreatic, esophageal, renal cancer or CNS cancer (e.g., glioma, glioblastoma). Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In some embodiments, this invention provides for the use of a compound as herein described, or its metabolite, pharmaceutically acceptable salt, pharmaceutical product, tautomer, polymorph, hydrate, isomer, N-oxide, prodrug or any combination thereof, for treating, suppressing, reducing the severity, reducing the risk, or inhibiting cancer in a subject. In another embodiment, the cancer is adrenocortical carcinoma, anal cancer, bladder cancer, brain tumor, brain stem tumor, breast cancer, drug-resistant breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, drug-resistant melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, drug-resistant ovarian cancer, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, drug-resistant prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, drug-resistant melanoma, small intestine cancer, soft tissue sarcoma, soft tissue sarcoma, testicular cancer, thymoma, malignant, thyroid cancer, urethral cancer, uterine cancer, drug-resistant uterine cancer, sarcoma, unusual cancer of childhood, vaginal cancer, vulvar cancer, Wilms' tumor, or any combination thereof. In another embodiment the subject has been previously treated with chemotherapy, radiotherapy or biological therapy.

In some embodiments, this invention provides for the use of a compound as herein described, or its metabolite, pharmaceutically acceptable salt, pharmaceutical product, tautomer, polymorph, hydrate, isomer, N-oxide, prodrug, or any combination thereof, for treating, suppressing, reducing the severity, reducing the risk, or inhibiting a metastatic cancer in a subject. In another embodiment, the cancer is adrenocortical carcinoma, anal cancer, bladder cancer, brain tumor, brain stem tumor, breast cancer, drug-resistant breast cancer, glioma, cerebellar astrocytoma, cerebral astrocytoma, ependymoma, medulloblastoma, supratentorial primitive neuroectodermal, pineal tumors, hypothalamic, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, drug-resistant melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, drug-resistant ovarian cancer, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, drug-resistant prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, drug-resistant melanoma, small intestine cancer, soft tissue sarcoma, soft tissue sarcoma, testicular cancer, thymoma, malignant, thyroid cancer, urethral cancer, uterine cancer, drug-resistant uterine cancer, sarcoma, unusual cancer of childhood, vaginal cancer, vulvar cancer, Wilms' tumor, or any combination thereof.

In some embodiments, this invention provides for the use of a compound as herein described, or its metabolite, pharmaceutically acceptable salt, pharmaceutical product, tautomer, polymorph, hydrate, isomer, N-oxide, prodrug, or any combination thereof, for treating, suppressing, reducing the severity, reducing the risk, or inhibiting a drug-resistant cancer or resistant cancer in a subject. In another embodiment, the cancer is adrenocortical carcinoma, anal cancer, bladder cancer, brain tumor, brain stem tumor, breast cancer, drug-resistant breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, drug-resistant melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, drug-resistant melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In one embodiment "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In one embodiment "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism. Thus, the resistance to anticancer agents used in chemotherapy is the main cause of treatment failure in malignant disorders, provoking tumors to become resistant. Drug resistance is the major cause of cancer chemotherapy failure.

In one embodiment "resistant cancer" refers to drug-resistant cancer as described herein above. In another embodiment "resistant cancer" refers to cancer cells that acquire resistance to any treatment such as chemotherapy, radiotherapy or biological therapy.

In one embodiment, this invention is directed to treating, suppressing, reducing the severity, reducing the risk, or inhibiting cancer in a subject, wherein the subject has been previously treated with chemotherapy, radiotherapy or biological therapy.

In one embodiment "chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In one embodiment, "radiotherapy" refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In one embodiment "biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

In one embodiment, this invention provides a method of treating a subject suffering from prostate cancer, metastatic prostate cancer, resistant prostate cancer or drug-resistant prostate cancer comprising the step of administering to said subject a compound of this invention, or its metabolite, pharmaceutically acceptable salt, pharmaceutical product, tautomer, hydrate, isomer, N-oxide, prodrug, polymorph, or any combination thereof, or a composition comprising the same in an amount effective to treat prostate cancer in the subject. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In one embodiment, this invention provides a method for suppressing, reducing the severity, reducing the risk, delaying the progression, or inhibiting prostate cancer, metastatic prostate cancer, resistant prostate cancer or drug-resistant prostate cancer in a subject, comprising administering to the subject a compound of this invention and/or its metabolite, pharmaceutically acceptable salt, pharmaceutical product, tautomer, hydrate, isomer, N-oxide, prodrug, polymorph, or any combination thereof or a composition comprising the same. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In one embodiment, this invention provides a method of treating a subject suffering from breast cancer, metastatic breast cancer, resistant breast cancer or drug-resistant breast cancer comprising the step of administering to said subject a compound of this invention, or its metabolite, pharmaceutically acceptable salt, pharmaceutical product, tautomer, hydrate, isomer, N-oxide, prodrug, polymorph, or any combination thereof, or a composition comprising the same. In another embodiment, the subject is a male or female. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In one embodiment, this invention provides a method of suppressing, reducing the severity, reducing the risk, delaying the progression, or inhibiting breast cancer, metastatic breast cancer, resistant breast cancer or drug-resistant breast cancer in a subject comprising the step of administering to said subject a compound of this invention or its metabolite, pharmaceutically acceptable salt, pharmaceutical product, tautomer, hydrate, isomer, N-oxide, prodrug, polymorph, or any combination thereof, or a composition comprising the same. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or its metabolite, pharmaceutically acceptable salt, pharmaceutical product, tautomer, hydrate, isomer, N-oxide, prodrug, polymorph, or any combination thereof, for treating, suppressing, reducing the severity, reducing the risk, delaying the progression, or inhibiting ovarian cancer, metastatic ovarian cancer, resistant ovarian cancer or drug-resistant ovarian cancer in a subject. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In one embodiment, this invention provides a method for treating, suppressing, reducing the severity, reducing the risk or inhibiting melanoma, metastatic melanoma, resistant melanoma or drug-resistant melanoma in a subject, comprising administering to the subject a compound of this invention and/or its metabolite, pharmaceutically acceptable salt, pharmaceutical product, tautomer, hydrate, isomer, N-oxide, prodrug, polymorph, or any combination thereof. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or its metabolite, pharmaceutically acceptable salt, pharmaceutical product, tautomer, hydrate, isomer, N-oxide, prodrug, polymorph, or any combination thereof, for treating, suppressing, reducing the severity, reducing the risk, delaying the progression, or inhibiting lung cancer, metastatic lung cancer, resistant lung cancer or drug-resistant lung cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting non-small cell lung cancer, metastatic small cell lung cancer, resistant small cell lung cancer or drug-resistant small cell lung cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting colon cancer, metastatic colon cancer, resistant colon cancer or drug-resistant colon cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting of leukemia, metastatic leukemia, resistant leukemia or drug-resistant leukemia. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting glioma, metastatic glioma, resistant glioma or drug-resistant glioma. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting lymphoma, metastatic lymphoma, resistant lymphoma or drug-resistant lymphoma. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting head and neck cancer, metastatic head and neck cancer, resistant head and neck cancer or drug-resistant head and neck cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting of pancreatic cancer, metastatic pancreatic cancer, resistant pancreatic cancer or drug-resistant pancreatic cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting esophageal cancer, metastatic esophageal cancer, resistant esophageal cancer or drug-resistant esophageal cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting renal cancer, metastatic renal cancer, resistant renal cancer or drug-resistant renal cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, this invention provides for the use of a compound as herein described, or metabolite, pharmaceutically acceptable salt, pharmaceutical product, tautomer, hydrate, isomer, N-oxide, prodrug, polymorph, any combination thereof, for treating, suppressing, reducing the severity, reducing the risk, delaying the progression, or inhibiting CNS cancer, metastatic CNS cancer, resistant CNS cancer or drug-resistant CNS cancer. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In some embodiments, this invention provides for the use of a compound as herein described, or its metabolite, pharmaceutically acceptable salt, pharmaceutical product, tautomer, polymorph, hydrate, isomer, N-oxide, prodrug or any combination thereof, for treating, suppressing, reducing the severity, reducing the risk, or inhibiting a drug resistant cancerous tumor or tumors in a subject. In another embodiment, the cancer is adrenocortical carcinoma, anal cancer, bladder cancer, brain tumor, brain stem tumor, breast cancer, drug-resistant breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, drug-resistant melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, drug-resistant melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, the tumor is prostate cancer tumor. In another embodiment, the tumor is a multidrug resistant (MDR) prostate cancer tumor. In another embodiment, the tumor is ovarian cancer tumor. In yet another embodiment, the tumor is a multidrug (MDR) resistant ovarian cancer tumor. In another embodiment, the tumor is uterine cancer tumor. In yet another embodiment, the tumor is a multidrug (MDR) resistant uterine cancer tumor. In another embodiment, the tumor is a melanoma tumor. In another embodiment, the tumor is a drug-resistant melanoma tumor. In another embodiment, the tumor is a multidrug resistant (MDR) melanoma tumor. In another embodiment, the tumor is a lung cancer tumor. In still another embodiment, the tumor is a colon cancer tumor. In another embodiment, the tumor is a breast cancer tumor. In another embodiment, the tumor is a drug-resistant breast cancer tumor. In another embodiment, the tumor is a glioma tumor. In another embodiment, the tumor is a leukemia tumor.

In one embodiment, this invention is directed to a method of destroying a cancerous cell comprising: providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture). In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33. In another embodiment, the cancer is selected from the group consisting of prostate cancer, drug-resistant prostate cancer, breast cancer, drug-resistant breast cancer, ovarian cancer, drug-resistant ovarian cancer, skin cancer, melanoma, drug-resistant melanoma, lung cancer, colon cancer, leukemia, glioma, renal cancer, CNS cancer, uterine cancer, drug-resistant uterine cancer, and combinations thereof.

In one embodiment, this invention is directed to a method of inhibiting, preventing, or slowing the progress of vascularization of a tumor comprising administering a compound of this invention to a subject having cancer under conditions effective to inhibit, prevent or slow the progress of vascularization of said tumor. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In one embodiment, this invention is directed to a method of inhibiting, preventing, or slowing the progress of vascularization of a metastatic tumor comprising administering a compound of this invention to a subject having cancer under conditions effective to inhibit, prevent or slow the progress of vascularization of said tumor. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In another embodiment, the tumor is selected from the group consisting of prostate cancer tumor, drug-resistant prostate cancer tumor, breast cancer tumor, drug-resistant breast cancer tumor, glioma tumor, ovarian cancer tumor, drug-resistant ovarian cancer tumor, skin cancer tumor, melanoma tumor, drug-resistant melanoma tumor, lung cancer tumor, colon cancer tumor, lymphoma tumor, renal cancer tumor, CNS cancer tumor, uterine cancer tumor, drug-resistant uterine cancer tumor, and combinations thereof.

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents. In one embodiment, the subject is human. In one embodiment, the subject is male. In another embodiment, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The compounds of the present invention are useful in the treatment or prevention of various forms of cancer, particularly prostate cancer, drug-resistant prostate cancer, breast cancer, drug-resistant breast cancer, ovarian cancer, drug-resistant ovarian cancer, skin cancer (e.g., melanoma), drug-resistant melanoma, lung cancer, colon cancer, glioma, leukemia, lymphoma, renal cancer, uterine cancer, drug-resistant uterine cancer, and CNS cancer (e.g., glioma, glioblastoma). Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

The compounds of the present invention are useful in the treatment, reducing the severity, reducing the risk, or inhibition of cancer, metastatic cancer, resistant cancer or drug-resistant cancer. In another embodiment, the cancer is prostate cancer, breast cancer, drug-resistant breast cancer, ovarian cancer, skin cancer (e.g., melanoma), drug-resistant melanoma, lung cancer, colon cancer, glioma, leukemia, lymphoma, head and neck, pancreatic, esophageal, renal cancer, uterine cancer or CNS cancer, or combinations thereof. Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention. In one embodiment, the compound is a compound of formula I-XV. In another embodiment, the compound is compound 4. In one embodiment, the compound is compound 5. In another embodiment, the compound is compound 6. In another embodiment, the compound is compound 7. In another embodiment, the compound is compound 14. In another embodiment, the compound is compound 15. In another embodiment, the compound is compound 18. In another embodiment, the compound is compound 33.

In one embodiment, the compound is administered in combination with an anti-cancer agent by administering the compounds as herein described, alone or in combination with other agents. In one embodiment, the compound is administered in combination with another cancer therapy (such as radiotherapy, chemotherapy, biological therapy).

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

The following examples are presented in order to more fully illustrate the embodiments of the invention. They should in no way, however, be construed as limiting the broad scope of the invention.

EXAMPLES

Example 1

Figure 2:
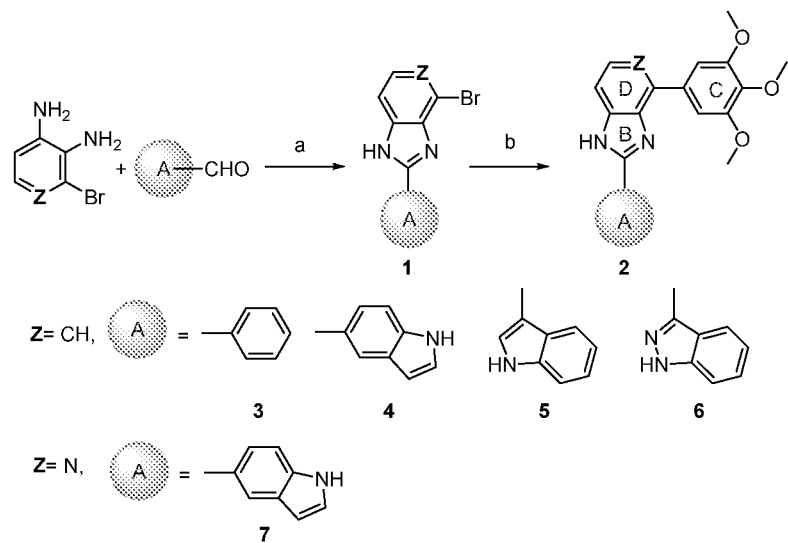
FIG. 2 depicts a synthetic scheme for the preparation of compounds of this invention. Reagents and conditions: a) TsOH, EtOH, reflux; b) (3,4,5-trimethoxyphenyl)boronic acid, $K_2CO_3$, $Pd(PPh_3)_4$.

Synthesis of Compounds of Formula I (FIG. 2)

Materials.

All reagents were purchased from Sigma-Aldrich Chemical Co., Fisher Scientific (Pittsburgh, Pa.), AK Scientific (Mountain View, Calif.), Oakwood Products (West Columbia, S.C.), etc. and were used without further purification. Moisture-sensitive reactions were carried under an argon atmosphere. Routine thin layer chromatography (TLC) was performed on aluminum backed Uniplates. (Analtech, Newark, Del.). Melting points were measured with Fisher-Johns melting point apparatus (uncorrected). NMR spectra were obtained on a Bruker AX 300 (Billerica, Mass.) spectrometer or Varian Inova-500 spectrometer. Chemical shifts are reported as parts per million (ppm) relative to TMS in $CDCl_3$. Mass spectral data was collected on a Bruker ESQUIRE electrospray/ion trap instrument in positive and negative ion modes. Elemental analyses were performed by Atlantic Microlab Inc., (Norcross, Ga.). Unless specified, all the tested compounds present >95% purity established through combustion analysis.

General Procedure for the Preparation of Compounds 3-7 (FIG. 2):

Different aldehydes, 3-bromobenzene-1,2-diamine (3 mmol), p-toluenesulfonic acid (0.3 mmol), and 15 mL of EtOH were refluxed for 24 h under argon atmosphere. The solvent was removed, 25 mL of water was added, and the mixture was extracted with EtOAc (3×50 mL). The combined organic layers were dried on $MgSO_4$, filtered and concentrated in vacuo. The residue was purified by flash chromatography to give the desired 4-bromo-2-substituted-1H-benzo[d]imidazole.

Corresponding bromides obtained from last step (1 eq), 3,4,5-trimethoxyphenylboronic acid (1 eq), THF (3 ml)/water (0.3 ml) solution of sodium carbonate (2 eq), and tetrakistriphenyl phosphinepalladium (0.1 eq) was refluxed overnight. After adding water to a reaction mixture, extracted with ethyl acetate. The organic layer was dried on $MgSO_4$, filtered and concentrated in vacuo. The residue was purified by flash chromatography to give desired fused "D" ring benzoimidazole compounds 3-6 or imidazo[4,5-c]pyridine compound 7 (FIG. 2).

2-Phenyl-4-(3,4,5-trimethoxyphenyl)-1H-benzo[d]imidazole (3)

$^1$H NMR ($CDCl_3$): 3.78, 3.93 (s, s, 6H), 3.91, 3.98 (s, s, 3H), 6.10, 6.82 (s, s, 2H), 7.29-8.08 (m, 8H), 9.70, 9.84 (s, br, 1H). MS (ESI) m/z 359.1 [M−H]$^-$, 361.4 [M+H]$^+$. Anal. ($C_{22}H_{20}N_2O_3$) C, H, N.

2-(1H-Indol-3-yl)-4-(3,4,5-trimethoxyphenyl)-1H-benzo[d]imidazole (4)

$^1$H NMR (DMSO-$d_6$): 3.76, 3.97 (s, s, 3H), 3.90, 3.97 (s, s, 6H), 6.96-7.62 (m, H), 7.62, 7.72 (s, s, 2H), 8.16, 8.42 (s, br, 1H), 8.58, 8.66 (d, d, 1H), 11.57, 11.64 (s, s, 1H), 12.16,

2-(1H-Indol-5-yl)-4-(3,4,5-trimethoxyphenyl)-1H-benzo[d]imidazole (5)

$^1$H NMR (DMSO-d$_6$): 3.73, 3.87 (s, s, 6H), 3.75, 3.92 (s, s, 3H), 5.70, 5.75 (s, s, 2H), 6.32, 6.49 (s, s, 1H), 6.54, 6.85 (d, d, 1H), 7.22-7.65 (m, 4H), 8.01, 8.42 (br, s, 2H), 11.09, 11.37 (s, s, 1H), 12.36, 12.84 (s, s, 1H). MS (ESI) m/z 398.1 [M−H]$^−$, 400.1 [M+H]$^+$. Anal. (C$_{24}$H$_{21}$N$_3$O$_3$) C, H, N.

3-(4-(3,4,5-Trimethoxyphenyl)-1H-benzo[d]imidazol-2-yl)-1H-indazole (6)

$^1$H NMR (DMSO-d$_6$): 3.76 (s, 3H), 3.95 (s, 6H), 6.65 (s, 1H), 6.93 (t, 1H), 7.34-7.34 (m, 2H), 7.45-7.57 (m, 4H), 7.63 (s, 2H), 7.70 (d, 1H), 8.75 (d, 1H), 12.96 (s, 1H), 13.77 (s, 1H). MS (ESI) m/z 399.1 [M−H]$^−$, 401.3 [M+H]$^+$. Anal. (C$_{23}$H$_{20}$N$_4$O$_3$) C, H, N.

2-(1H-Indol-5-yl)-4-(3,4,5-trimethoxyphenyl)-1H-imidazo[4,5-c]pyridine (7)

$^1$H NMR (DMSO-d$_6$): 3.77 (s, 3H), 3.96 (s, 6H), 6.61 (s, 1H), 7.46-7.48 (m, 2H), 7.59 (d, 1H), 8.08 (dd, 1H), 8.36 (d, 1H), 8.41 (s, 2H), 8.49 (s, 1H), 11.44 (s, 1H), 13.26 (s, 1H). MS (ESI) m/z 399.0 [M−H]$^−$, 401.3 [M+H]$^+$. Anal. (C$_{23}$H$_{20}$N$_4$O$_3$) C, H, N.

Example 2

Synthesis of Compounds of Formula XI (FIG. 3)

(4-Hydroxy-3,5-dimethoxyphenyl)(2-phenylthiazol-4-yl)methanone (11)

Intermediates 8-10 were prepared from benzonitrile and cysteine following the same procedure as described in Lu, Y.; Li, C. M.; Wang, Z.; Ross, C. R., 2nd; Chen, J.; Dalton, J. T.; Li, W.; Miller, D. D. Discovery of 4-substituted methoxybenzoyl-aryl-thiazole as novel anticancer agents: synthesis, biological evaluation, and structure-activity relationships. *J Med Chem* 2009, 52(6), 1701-11. Compound 10 [a "SMART" (4-substituted methoxybenzoyl-aryl-thiazole) template compound] (500 mg, 1.4 mmol) was dissolved in CH$_2$Cl$_2$ (50 mL) at RT under argon protection. Anhydrous AlCl$_3$ (374 mg, 2.8 mmol) was added, and the reaction mixture stirred for 12 h. The reaction was quenched with H$_2$O (30 mL), the organic phase separated, and the aqueous phase extracted with CH$_2$Cl$_2$ (2×20 mL). The combined organic phases were washed with brine, dried over Mg$_2$SO$_4$, filtered, and concentrated to dryness under reduced pressure. Compound 11 (410 mg, 85.9% yield) was obtained after flash column purification using hexanes-EtOAc system. $^1$H NMR (CDCl$_3$): 4.00 (s, 6H), 6.02 (s, 1H), 7.47-7.48 (m, 3H), 7.91 (s, 2H), 8.01-8.03 (m, 2H), 8.27 (s, 1H). MS (ESI) m/z 339.9 [M−H]$^−$, 364.1 [M+Na]$^+$. Anal. (C$_{18}$H$_{15}$NO$_4$S) C, H, N.

2,6-Dimethoxy-4-(2-phenylthiazole-4-carbonyl)phenyl 2-chloroacetate (12)

At 0° C., 2-chloroacetyl chloride (100 mg, 0.9 mmol) was added to a solution of 11 (100 mg, 0.29 mmol) in CH$_2$Cl$_2$ (30 mL). Then triethylamine (44 mg, 0.44 mmol) was charged in the mixture and stirred until starting material disappeared on TLC. The reaction mixture was quenched with H$_2$O (10 mL), the organic phase separated, and the aqueous phase extracted with CH$_2$Cl$_2$ (2×10 mL). The combined organic phases were washed with brine, dried over Mg$_2$SO$_4$, filtered, and concentrated to dryness under reduced pressure. Compound 12 (99 mg, 81.7% yield) was obtained after flash column purification using hexanes-EtOAc system. M.P. 147-148° C. $^1$H NMR (CDCl$_3$): 3.92 (s, 6H), 4.42 (s, 2H), 7.47-7.49 (m, 3H), 7.82 (s, 2H), 8.00-8.02 (m, 2H), 8.32 (s, 1H). MS (ESI) m/z 418.1 [M−H]$^−$. Anal. (C$_{20}$H$_{16}$ClNO$_5$S) C, H, N.

2,6-Dimethoxy-4-(2-phenylthiazole-4-carbonyl)phenyl 2,2,2-trifluoroacetate (13)

At 0° C., trifluoroacetyl anhydride (189 mg, 0.9 mmol) was added to a solution of 11 (100 mg, 0.29 mmol) in CH$_2$Cl$_2$ (10 mL). Then DMAP (54 mg, 0.44 mmol) was charged in the mixture and stirred at RT until starting material disappeared on TLC. The reaction mixture was quenched with H$_2$O (10 mL), the organic phase separated, and the aqueous phase extracted with CH$_2$Cl$_2$ (2×10 mL). The combined organic phases were washed with brine, dried over Mg$_2$SO$_4$, filtered, and concentrated to dryness under reduced pressure. Compound 13 (89 mg, 70.2% yield) was obtained after flash column purification using hexanes-EtOAc system. M. p. 151-153° C. $^1$H NMR (CDCl$_3$): 3.94 (s, 6H), 7.48-7.49 (m, 3H), 7.84 (s, 2H), 8.00-8.02 (m, 2H), 8.34 (s, 1H). MS (ESI) m/z 438.1 [M+H]$^+$. Anal. (C$_{20}$H$_{164}$F$_3$NO$_5$S) C, H, N.

(4-(Benzyloxy)-3,5-dimethoxyphenyl)(2-phenylthiazol-4-yl)methanone (14)

Under an argon atmosphere, potassium carbonate (49 mg, 0.352 mmol) and benzyl bromide (33 mg, 0.194 mmol) were added to a solution of 11 (60 mg, 0.176 mmol) in 10 mL of dry DMF. The mixture was stirred for 1 h at 100° C. and then transferred into water (10 mL). The compound 14 was extracted with EtOAc, washed with distilled water, dried on magnesium sulfate, and concentrated under vacuum using a rotary evaporator. The crude oily product was purified by flash column and white solid 14 (51 mg) was obtained. Yield=67.2%. M. p. 119-120° C. $^1$H NMR (CDCl$_3$): 3.92 (s, 6H), 5.15 (s, 2H), 7.29-7.37 (m, 3H), 7.48-7.51 (m, 5H), 7.79 (s, 2H), 8.01-8.02 (m, 2H), 8.28 (s, 1H). MS (ESI) m/z 432.1 [M+H]$^+$. Anal. (C$_{25}$H$_{21}$NO$_4$S) C, H, N.

(3,5-Dimethoxy-4-(methoxymethoxy)phenyl)(2-phenylthiazol-4-yl)methanone (15)

At 0° C., MOMCl (27 mg, 0.33 mmol) was added to a solution of 11 (75 mg, 0.22 mmol) in CH$_2$Cl$_2$ (10 mL). Then Hunig's base (57 mg, 0.44 mmol) was charged in the mixture and stirred at RT until starting material disappeared on TLC. The reaction mixture was quenched with H$_2$O (10 mL), the organic phase separated, and the aqueous phase extracted with CH$_2$Cl$_2$ (2×10 mL). The combined organic phases were washed with brine, dried over Mg$_2$SO$_4$, filtered, and concentrated to dryness under reduced pressure. Compound 15 (83 mg, 98.0% yield) was obtained as yellow crystals after flash column purification using hexanes-EtOAc system. M. p. 103-104° C. $^1$H NMR (CDCl$_3$): 3.62 (s, 3H), 3.95 (s, 6H), 5.26 (s, 2H), 7.47-7.49 (m, 3H), 7.80 (s, 2H), 8.01-8.03 (m, 2H), 8.28 (s, 1H). MS (ESI) m/z 408.1 [M+Na]$^+$. Anal. (C$_{20}$H$_{19}$NO$_5$S) C, H, N.

2-(2-(2,6-Dimethoxy-4-(2-phenylthiazole-4-carbonyl)phenoxy)ethyl)isoindoline-1,3-dione (17)

To a solution of 11 (200 mg, 0.59 mmole) and 2-(2-bromoethyl)isoindoline-1,3-dione (223 mg, 0.88 mmol) in DMF (2.5 ml) was added $K_2CO_3$ (97 mg, 0.7 mmol) and stirred the reaction mixture at 120° C. for overnight. Then the reaction mixture was quenched in water and extracted with ethyl acetate. The organic layer was concentrated and further purified by column chromatography to get 132 mg of pure desired product 17. Yield=43.5%. M. p. 148-150° C. $^1$H NMR (CDCl$_3$) δ 3.71 (s, 6H), 4.14 (t, 2H, J=5.5 Hz), 4.41 (t, 2H, J=5.5 Hz), 7.49-7.51 (m, 3H), 7.70 (s, 2H), 7.75 (q, 2H, J=3.0 Hz), 7.91 (q, 2H, J=3.0 Hz), 8.01-8.03 (m, 2H), 8.27 (s, 1H). MS (ESI) m/z 537.1 [M+Na]$^+$. Anal. ($C_{28}H_{22}N_2O_6S$) C, H, N.

(4-(2-Aminoethyl)-3,5-dimethoxyphenyl)(2-phenylthiazol-4-yl)methanone (18)

To a solution of 11 (23 mg, 0.07 mmole) and tert-butyl (2-bromoethyl)carbamate (23 mg, 0.1 mmol) in DMF (2.5 ml) was added $Cs_2CO_3$ (46 mg, 0.2 mmol) and the reaction mixture was stirred for 3 days at RT until TLC showed that the reaction had finished. Then the reaction mixture was quenched in ice cold water and extracted with ethyl acetate. The organic layer was concentrated and further purified by column chromatography to get 22 mg of pure desired product tert-butyl (2-(2,6-dimethoxy-4-(2-phenylthiazole-4-carbonyl)phenoxy)ethyl)carbamate 16. Yield=65.1%. MS (ESI) m/z 483.9 [M–H]$^-$, 485.1 [M+H]$^+$. Boc protected compound 16 was added to a solution of HCl in dioxane (4M) and stirred for overnight. The precipitate was collected and washed with diethyl ether to afford HCl salts of 18. $^1$H NMR (Acetone-d$_6$): 3.09-3.13 (q, 2H, J=5.5 Hz), 3.79 (br, 2H), 3.90 (s, 6H), 4.17 (t, 2H, J=5.5 Hz), 7.55-7.58 (m, 3H), 7.66 (s, 2H), 8.02-8.04 (m, 2H), 8.68 (s, 1H). MS (ESI) m/z 385.1 [M+H]$^+$. Anal. ($C_{20}H_{20}N_2O_3S$) C, H, N.

Example 3

Figure 4:
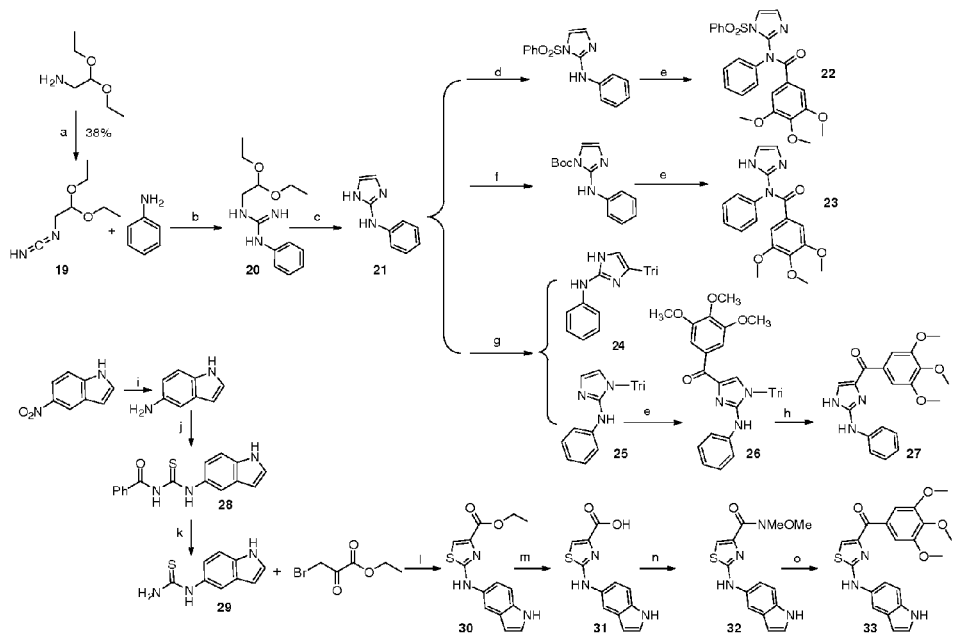
FIG. 4 depicts a synthetic scheme for the preparation of phenyl-amino-thiazole/imidazole analogues. Reagents and conditions: (a) BrCN, $Et_2O$/hexane; (b) $CH_3SO_3H$, EtOH, reflux, 24 h; (c) (1) 6M HCl, (2) NaOH 25% conc.; (d) $PhSO_2Cl$, $Et_3N$; (e) $-78°$ C., t-BuLi, 3,4,5-trimethoxybenzoyl chloride; (f) $Boc_2O$, NaOH; (g) (chloromethanetriyl)tribenzene, $Et_3N$, $CH_2Cl_2$; (h) HCl; (i) $H_2$, Pd—C, 5%, EtOH, 40 psi; (j) PhCOSCN, $Me_2CO$; (k) MeOH, 1N NaOH; (l) EtOH, $65°$ C.; (m) NaOH, MeOH; (n) HBTU, NMM, $HNCH_3OCH_3 \cdot HCl$, $CH_2Cl_2$; (o) 3,4,5-trimethoxyphenylbromide, n-BuLi, THF.

Synthesis of Phenyl-Amino-Thiazole/Imidazole Compounds (FIG. 4)

N-Phenyl-1H-imidazol-2-amine (21)

At 0° C., to a solution of the amino-acetaldehyde diethyl acetal (2.66 g, 20 mmol) in diethyl ether/hexane mixture (20 mL, 1:1) was added BrCN (2.11 g, 20 mmol) in small portions. The reaction mixture was stirred at RT overnight. The solid was removed by filtration and washed with ether. The combined filtrate was concentrated. Purification by flash column chromatography (silica gel, eluting with dichloromethane to 5% methanol in dichloromethane, gradient) afforded N-(2, 2-diethoxyethyl)carbodiimide 19. $^1$H NMR 500 MHz (CDCl$_3$): 1.23 (t, 6H, J=7.0 Hz), 3.16 (t, 2H, J=6.0 Hz), 3.56 (dt, 2H), 3.64 (br, s, 1H), 3.73 (dt, 2H), 4.58 (t, J=5.0 Hz, 1H). MS (ESI) m/z 156.8 [M–H]$^-$, 180.9 [M+Na]$^+$. Aniline (1.66 g, 17.8 mmol) was dissolved in ethanol (50 mL), and a solution of 19 (2.82 g, 17.8 mmol) in 5 mL diethyl ether was added dropwise. Methanesulfonic acid (1.71 g, 17.8 mmol) was then added, and the mixture was refluxed for 24 h. The reaction mixture was poured into NaOH (0.5 M) and extracted with $CH_2Cl_2$. Drying with MgSO$_4$ and concentrated in vacuo afforded a product that was subjected to flash chromatography to give the intermediate guanidine 20 (3.3 g, 73.8%). The guanidine (3 g, 12 mmoL) was dissolved in HCl (5 mL, 6 M) at 0° C. and then stirred for 2 h. After the starting material was consumed, NaOH (25%) was added until a precipitate formed (pH 14). This mixture was stirred for 30 min. The reaction was then poured into NaOH (0.5 M), extracted with $CH_2Cl_2$, dried, and concentrated. Flash chromatography afforded 21 (1.16 g, 61%). $^1$H NMR (DMSO-d$_6$): 6.68 (s, 2H), 6.75 (m, 1H), 7.17 (m, 2H), 7.34 (m, 2H), 8.58 (s, 1H). MS (ESI) m/z 157.6 [M–H]$^-$, 160.0 [M+H]$^+$.

3,4,5-Trimethoxy-N-phenyl-N-(1-(phenylsulfonyl)-1H-imidazol-2-yl)benzamide (22)

To a solution of N-phenyl-1H-imidazol-2-amine 21 (40 mg, 0.25 mmol) in $CH_2Cl_2$ (10 mL) was added benzenesulfonyl chloride (441 mg, 2.5 mmoL) and triethylamine (252 mg, 2.5 mmol). Reaction mixture was stirred overnight at room temperature. The reaction mixture was quenched by sat. NH$_4$Cl and extracted with $CH_2Cl_2$. Drying with MgSO$_4$ and concentrated in vacuo afforded a product that was subjected to flash chromatography to give benzenesulfonyl protected intermediate (79 mg, 72%). This intermediate was dissolved in THF and cooled down to −78° C., and then t-BuLi (1.7M) was charged under Ar$_2$. After stirred for an hour, 3,4,5-trimethoxybenzoyl chloride (47 mg, 0.26 mmoL) was added and stirred overnight. The reaction mixture was poured into NH$_4$Cl (Sat.) and extracted with ethyl acetate. Drying with MgSO$_4$ and concentrated in vacuo afforded a crude product that was purified by flash chromatography to give 22 (35%). $^1$H NMR (CDCl$_3$): 3.78 (s, 6H), 3.87 (s, 3H), 6.91 (s, 2H), 6.97 (s, 1H), 7.18 (m, 2H), 7.20 (d, 1H), 7.25 (m, 2H), 7.38 (m, 2H), 7.40 (d, 1H), 7.54 (br, 1H), 7.59 (t, 2H). MS (ESI) m/z 491.9 [M–H]$^-$, 516.1 [M+Na]$^+$.

N-(1H-imidazol-2-yl)-3,4,5-trimethoxy-N-phenylbenzamide (23)

To a solution of N-phenyl-1H-imidazol-2-amine 21 (900 mg, 5.66 mmoL) in dioxane and water (30 mL, 3:1) was added Boc$_2$O (2.68 g, 12.3 mmoL) and NaOH (0.6 g, 15 mmol) and stirred for 4 hs. The mixture was concentrated in vacuo and the residue was purified by flash chromatography to obtain the Boc protected intermediate. This intermediate (130 mg, 0.502 mmol) was dissolved in THF and cooled down to −78° C., and then t-BuLi (0.65 mL, 1.7M, 1.1 mmol) was charged under Ar$_2$. After stirred for an hour, 3,4,5-trimethoxybenzoyl chloride (116 mg, 0.502 mmoL) was added and stirred overnight. The reaction mixture was poured into NH$_4$Cl (Sat.) and extracted with ethyl acetate. Drying with MgSO$_4$ and concentrated in vacuo afforded a crude product that was purified by flash chromatography to give 23 (35%). $^1$H NMR (CDCl$_3$): 3.65 (s, 6H), 3.79 (s, 3H), 6.56 (s, 2H), 6.90 (m, 2H), 7.27-7.39 (m, 5H), 11.17 (br, 1H). MS (ESI) m/z 351.8 [M–H]$^-$, 376.3 [M+Na]$^+$.

N-Phenyl-4-trityl-1H-imidazol-2-amine (24) and N-phenyl-1-trityl-1H-imidazol-2-amine (25)

To a solution of N-phenyl-1H-imidazol-2-amine 21 (159 mg, 10 mmol) in triethylamine and $CH_2Cl_2$ stirring under an inert atmosphere at 0° C., was added (chloromethanetriyl)tribenzene (5 eq). The solution was allowed to warm to RT and stir until completed by TLC. The reaction mixture was then concentrated in vacuo, quenched with saturated aqueous sodium bicarbonate and extracted with ethyl acetate. Then dried with magnesium sulfate, and concentrated in vacuo. The resulting residue was purified by flash chromatography to give two different protected products. 24: $^1$H NMR (DMSO-d$_6$): 6.0 (s, 1H), 6.75 (m, 1H), 7.29-7.62 (m, 19H), 8.65 (s, 1H), 10.62 (s, 1H). MS (ESI) m/z 399.9 [M−H]$^−$, 403.1 [M+H]$^+$. 25: $^1$H NMR (DMSO-d$_6$): 6.08 (s, 1H), 6.41 (s, 1H), 6.85 (s, 1H), 7.13-7.52 (m, 20H), 8.65 (s, 1H), 10.62 (s, 1H). MS (ESI) m/z 399.8 [M−H]$^−$, 402.8 [M+H]$^+$.

(2-(Phenylamino)-1-trityl-1H-imidazol-4-yl)(3,4,5-trimethoxyphenyl)methanone (26)

To a solution of N-phenyl-1-trityl-1H-imidazol-2-amine 25 (116 mg, 0.289 mmol) in THF (10 mL) stirring under an inert atmosphere at −78° C., was added t-BuLi (0.34 mL, 1.7M, 0.58 mmol) and trimethoxybenzoyl chloride (66.5 mg, 0.289 mmoL). The reaction mixture was reacted for overnight, then quenched by NH$_4$Cl (Sat.) and extracted with ethyl acetate. Drying with MgSO$_4$ and concentrated in vacuo afforded a crude product that was purified by flash chromatography to give 26 (75 mg, 43.7%). $^1$H NMR (DMSO-d$_6$): 3.71, (s, 3H), 3.78 (s, 6H), 5.87 (s, 1H), 6.94 (s, 2H), 7.18-7.58 (m, 21H). MS (ESI) m/z 594.2 [M−H]$^−$, 596.3 [M+H]$^+$.

(2-(Phenylamino)-1H-imidazol-4-yl)(3,4,5-trimethoxyphenyl)methanone (27)

(2-(Phenylamino)-1-trityl-1H-imidazol-4-yl) (3,4,5-trimethoxyphenyl)methanone was dissolved in a solution of HCl in diethyl ether (2M) and stirred overnight. Saturated NaHCO$_3$ solution was then added and the reaction mixture was extracted three times with ether. The combined organic layers were dried (sodium sulfate), filtered and concentrated in vacuo. The residue was purified by flash chromatography to give pure 27. $^1$H NMR (DMSO-d$_6$): 3.73 (s, 3H), 3.82 (s, 6H), 6.62 (s, 2H), 7.02 (s, 2H), 7.33 (d, 2H), 7.43-7.51 (m, 3H), 7.54 (br, 1H). MS (ESI) m/z 352.1 [M−H]$^−$, 354.3 [M+H]$^+$. Anal. (C$_{19}$H$_{19}$N$_3$O$_4$) C, H, N.

N-((1H-Indol-5-yl)carbamothioyl)benzamide (28)

A mixture of 5-nitro-1H-indole (11 g, 67.9 mmol) and Pd/C (5%; 1 g), dissolved in ethanol (50 mL), was hydrogenated for 3 h at 40 psi. The reaction mixture was filtered and the excess of ethanol was evaporated under reduced pressure. Solid product was recrystallized from hexane to obtain the pure compound 5-aminoindole. Yield: 92.5%. $^1$H NMR (500 MHz, CDCl$_3$): δ 3.50 (s, 2H), 6.37 (s, 1H), 6.67 (dd, 1H), 6.95 (s, 1H), 7.13 (s, 1H), 7.20 (d, 1H), 7.96 (br, 1H). MS (ESI) m/z 133.0 (M+H)$^+$. A solution of 5-aminoindole (8 g, 60.6 mmol) in acetone (150 mL) was reacted with benzoylisothiocyanate (9.88 g, 60. mmol) at RT for about 4 h until TLC showed reaction finished to yield compound 28. $^1$H NMR (300 MHz, CDCl$_3$): δ 6.61 (br, 1H), 7.26-7.28 (d, 1H), 7.38-7.45 (m, 2H), 7.54-7.59 (m, 2H), 7.65-7.70 (m, 1H), 7.91-7.94 (m, 2H), 7.98 (s, 1H), 8.27 (s, br, 1H), 9.12 (s, 1H), 12.51 (s, 1H). MS (ESI) m/z 318.1 [M+Na]$^+$.

2-(1H-Indol-5-ylamino)-N-methoxy-N-methylthiazole-4-carboxamide (32)

The resulting solid 28 was filtered and treated with 2 N NaOH in THF (120 mL). The mixture was refluxed for about 6 h and allowed to warm to RT. The solvent was evaporated off under vacuum. The residue was diluted with water (20 mL) and neutralized to pH 7 with 1N HCl. The resulting solid was filtered and dried under vacuum to afford 5-indolylthiourea (29). Compound 29 (0.01 mol) and ethyl bromopyruvate (0.011 mol) were dissolved in 3 mL ethanol and held at reflux for 2 h. The reaction was cooled, the crystalline ethyl 2-(1H-indol-5-ylamino)thiazole-4-carboxylate (30) was collected by filtration and washed with ethanol. Refluxing the mixture of ethyl esters with the NaOH-ethanol solution gave 2-(1H-indol-5-ylamino)thiazole-4-carboxylic acid (31) which was used directly in the next steps. To a mixture of the crude acid (2.5 mmol), HBTU (2.6 mmol) and NMM (5.3 mmol) in CH$_2$Cl$_2$ (30 mL) was added HCl salt of HNCH$_3$OCH$_3$ (2.6 mmol) and stirring continued at RT for overnight. The reaction mixture was diluted with CH$_2$Cl$_2$ (20 mL) and sequentially washed with water, satd. NaHCO$_3$, brine and dried over MgSO$_4$. The solvent was removed under reduced pressure to yield a crude product, which was purified by column chromatography to obtain pure Weinreb amide 2-(1H-indol-5-ylamino)-N-methoxy-N-methylthiazole-4-carboxamide (32) (45.6% yield for overall 5 steps). $^1$H NMR (CDCl$_3$): 3.42 (s, 3H), 3.77 (s, 3H), 6.54 (m, 1H), 7.26 (m, 1H), 7.29 (m, 2H), 7.40 (d, 2H), 7.61 (m, 1H), 8.30 (br, 1H). MS (ESI) m/z 303.0 [M+H]$^+$.

(2-((1H-Indol-5-yl)amino)thiazol-4-yl)(3,4,5-trimethoxyphenyl)methanone (33)

At −78° C., to a solution of 5-bromo-1,2,3-trimethoxybenzene (1.235 g, 5.0 mmol) in 30 mL THF was charged n-BuLi in hexane (2.5N, 2.4 mL, 6 mmol) under Ar$_2$ protection and stirred for 10 min. Weinreb amide 32 (1 mmol) in 10 mL THF was added to lithium reagent and allowed to stir at RT for 2 h. The reaction mixture was quenched with satd. NH$_4$Cl, extracted with ethyl ether, dried with MgSO$_4$ The solvent was removed under reduced pressure to yield a crude product, which was purified by column chromatography to obtain pure 33 (51.7% yield). $^1$H NMR (300 MHz, CDCl$_3$) δ 3.89 (s, 6H), 3.93 (s, 3H), 6.55 (m, 1H), 7.15-7.12 (m, 1H), 7.28-7.26 (m, 1H), 7.36 (s, 1H), 7.39 (s, 1H), 7.46 (s, 2H), 7.68 (d, 1H), 8.29 (br, 1H). MS (ESI) m/z 432.1 (M+Na)$^+$, 408.0 (M−H)$^−$. Anal. (C$_{23}$H$_{19}$N$_3$O$_4$S) C, H, N.

Example 4

Molecular Modeling of the Compounds of this Invention

Molecular Modeling.

The molecular modeling studies were performed with the published crystal structures of the α,β-tubulin dimer in complex with DAMA-colchicine (Protein Data Bank code 1SA0). Schrodinger Molecular Modeling Suite 2013 (Schrodinger Inc., Portland, Oreg.) was used for the modeling studies with procedures similar to those described before Chen, J. et al. *Bioorg Med Chem* 2011, 19(16), 4782-95; Slominski, A. T. et al. *The Journal of Steroid Biochemistry and Molecular Biology* 2013, 137, 107-23; Xiao, M et al. *J Med Chem* 2013, 56(8), 3318-29; Chen, J. et al. *J Med Chem* 2012, 55(16), 7285-9. Briefly, the structures of the protein-ligand complexes were prepared using the Protein Preparation module, and the active ligand binding sites were defined based on the native ligand. Both native ligand DAMA-colchicine and the designed tubulin inhibitors described in this study were built and prepared for docking using the Ligprep module before they were docked into 1SA0. The Glide docking score obtained from this modeling approach is an estimation of the binding energy (kcal/mol) when a ligand binds to the tubulin dimer. A lower (more negative) number suggests more favorable binding interaction between a ligand and the receptor. Data analyses were performed using the Maestro interface of the software.

Figure 6:
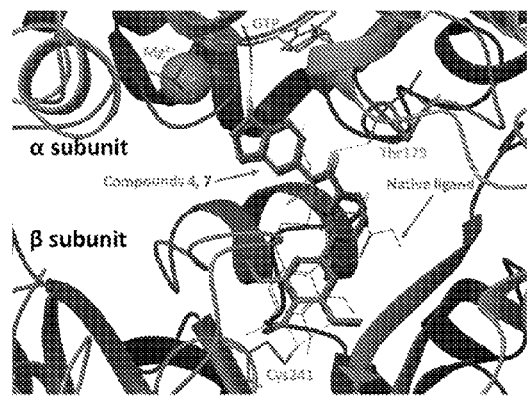
FIG. 6 depicts potential binding poses for compound 4 (tube model, Glide docking score −8.58) and 7 (tube model, Glide docking score −8.10) in tubulin α,β-dimer (PDB code: 1SA0). The native ligand, DAMA-colchicine (Glide docking score of −9.26) is shown in thin wire model.

Compounds 4 and 7 were docked into the colchicine binding site in tubulin (FIG. 6, PDB code: 1SA0), and showed very similar binding poses that overlapped with the native ligand reasonably well. As anticipated, the trimethoxy moiety in 4 or 7 occupied the pocket of the trimethoxy moiety in the native ligand (DAMA-colchicine), but showed some shifting in its position. This slight shift positioned the oxygen atoms in two methoxy groups of 4 and 7 to be close to Cys-241 of the β-subunit and allowed the formation of two hydrogen bonds (dotted lines). The NH of the imidazole moiety in 4 or 7 formed another hydrogen bond to Thr-179 in the α-subunit as shown in FIG. 6. Interestingly, due to the formation planar structure in the middle portion of 4 or 7, the 5-indolyl moiety changed orientation to reach toward the GTP in the α-subunit. The Glide docking scores for 4 (−8.58) and 7 (−8.10) were comparable with that of the native ligand, DAMA-colchicine (−9.26) based on this modeling calculation, suggesting they may have comparable effects in tubulin binding.

The cytotoxic potential of the anti-tubulin compounds was evaluated using the sulforhodamine B (SRB) assay after 96 h of treatment.

Results:

From the proliferative activity data compared to compound 10, the unsubstituted compound of the SMART template, most of the benzo-imidazoles 3-6 showed only moderate activity; except 4, which has a 5-indolyl at the A ring position, which showed comparable potency against tested melanoma and prostate cancer cell lines. (See Table 1) For further modification, 5-indolyl was retained at the A ring, pyridine-fused imidazole was utilized to replace the benzo-imidazole, and yielded 7. This compound showed increased potency compared to both 10 and 4. The $IC_{50}$ values improved by at least 5 fold against melanoma A375 cells and androgen sensitive prostate cancer LNCaP cells. Further these novel fused ring templates blocked the potential phase I metabolic reactions caused by ketone reduction in 10 (Example 6).

TABLE 1

Antiproliferative activities of analogues with a fused D-ring template

| | | | $IC_{50} \pm SEM$ (μM) | | | | |
| | | | Melanoma cells | | Prostate Cancer cells | | |
| | Z | A | A375 | DU 145 | PC-3 | LNCaP | PPC-1 |
|---|---|---|---|---|---|---|---|
| 3 | CH | Ph | ND | 7.8 ± 0.4 | 2.4 ± 0.6 | 2.1 ± 0.3 | 2.1 ± 0.4 |
| 4 | CH | 5-indolyl | 0.025 ± 0.004 | 0.057 ± 0.005 | 0.022 ± 0.009 | 0.028 ± 0.003 | 0.02 ± 0.01 |
| 5 | CH | 3-indolyl | 0.6 ± 0.1 | 4.2 ± 0.3 | 0.9 ± 0.2 | 0.8 ± 0.1 | 1.3 ± 0.3 |
| 6 | CH | 3-indazolyl | 1.1 ± 0.2 | 4.0 ± 0.1 | 0.8 ± 0.1 | 1.6 ± 0.1 | 1.0 ± 0.1 |
| 7 | N | 5-indolyl | 0.005 ± 0.001 | ND | 0.006 ± 0.002 | 0.005 ± 0.002 | 0.042 ± 0.003 |
| 10 (SMART) | — | — | 0.028 ± 0.005 | 0.071 ± 0.004 | 0.021 ± 0.001 | 0.028 ± 0.004 | 0.043 ± 0.005 |

Example 5

Prostate Cancer and Melanoma Activity of the Compounds of this Invention

Cell Culture and Cytotoxicity Assay of Prostate Cancer and Melanoma.

All cell lines were obtained from ATCC (American Type Culture Collection, Manassas, Va., USA), while cell culture supplies were purchased from Cellgro Mediatech (Herndon, Va., USA). We examined the antiproliferative activity of our anti-tubulin compounds in four human prostate cancer cell lines (LNCaP, DU 145, PC-3, and PPC-1) and three melanoma cell lines (A375, B16-F1 and WM-164). All prostate cancer cell lines were cultured in RPMI 1640, supplemented with 10% fetal bovine serum (FBS). Melanoma cells were cultured in DMEM, supplemented with 5% FBS, 1% antibiotic/antimycotic mixture (Sigma-Aldrich, Inc., St. Louis, Mo., USA) and bovine insulin (5 μg/ml; Sigma-Aldrich).

Compound 15 showed improved activity compared to trimethoxy benzoyl compound 10 (i.e. 20 nM (15) vs. 28 nM (10) against A375 cells; Table 2). This discovery supported the hypothesis that the para position of the benzoyl ring is a tolerant location for further modification. The two atom extension (—OCH$_2$—) of 15 was still potent. However, the idea of alkylation at p-position did not work as expected on the inhibition of cancer cell growth. From the result shown in Table 2, the potency of alkylating agent 12 dropped significantly against both melanoma and prostate cancer cells. 13 and 14 showed similar trends on activity as 12. 17 with a phthalimide protection group showed micromolar range potency. Introducing an ethyl amine (18) at the p-position remained moderate in activity with hundreds of nanomolar $IC_{50}$s, but it still was less potent than the trimethoxy benzoyl compound 10.

TABLE 2

Antiproliferative activities of analogues with modified para-position of benzoyl ring

| | R | IC$_{50}$ ± SEM (μM) | | | | | |
|---|---|---|---|---|---|---|---|
| | | Melanoma cells | | Prostate Cancer cells | | | |
| | | B16-F1 | A375 | DU 145 | PC-3 | LNCaP | PPC-1 |
| 12 | OCOCH$_2$Cl | 3.2 ± 1.2 | 10.8 ± 4.4 | >10 | >10 | >10 | >10 |
| 13 | OCOCF$_3$ | 8.9 ± 2.8 | 22.2 ± 8.5 | >10 | >10 | >10 | >10 |
| 14 | OCH$_2$Ph | 10.6 ± 3.2 | >10 | >10 | >10 | >10 | >10 |
| 15 | OCH$_2$OCH$_3$ | 0.019 ± 0.005 | 0.020 ± 0.005 | 0.112 ± 0.01 | 0.017 ± 0.00 | 0.031 ± 0.00 | 0.022 ± 0.005 |
| 17 | OCH$_2$CH$_2$Phth | 1.3 ± 0.3 | 3.1 ± 0.5 | 0.6 ± 0.2 | >10 | 1.4 ± 0.8 | 0.6 ± 0.2 |
| 18 | OCH$_2$CH$_2$NH$_2$ | 0.142 ± 0.015 | 0.527 ± 0.022 | 0.464 ± 0.03 | 0.158 ± 0.03 | 0.117 ± 0.06 | 0.184 ± 0.02 |
| 10 | OCH$_3$ | 0.055 ± 0.005 | 0.028 ± 0.005 | 0.071 ± 0.004 | 0.021 ± 0.001 | 0.028 ± 0.004 | 0.043 ± 0.005 |

* "Phth" refers to phthalimide.

Table 3 presents results of analogue compounds, wherein 27 did not demonstrate any activity against all tested cell lines. 33 showed excellent growth inhibition for both prostate cancer and melanoma cells in vitro. The IC$_{50}$s were increased 2-3 fold on prostate cancer cells compared to PAT.

1.2 mL containing 1 mg/mL microsomal protein in reaction buffer [0.2 M of phosphate buffer solution (pH 7.4), 1.3 mM NADP$^+$, 3.3 mM glucose-6-phosphate, and 0.4 U/mL glucose-6-phosphate dehydrogenase] at 37° C. in a shaking incubator. Pooled human liver microsomes were utilized to

TABLE 3

Antiproliferative activities of modified A ring compounds

| | X | n = | Ar | IC$_{50}$ ± SEM (μM) | | | | | |
|---|---|---|---|---|---|---|---|---|---|
| | | | | Melanoma cells | | Prostate Cancer cells | | | |
| | | | | B16-F1 | A375 | DU 145 | PC-3 | LNCaP | PPC-1 |
| 27 | N | 1 | Ph | >30 | >30 | >30 | >30 | >30 | >30 |
| 33 | S | 1 | 5-indolyl | 0.084 ± 0.016 | 0.025 ± 0.006 | 0.024 ± 0.005 | 0.012 ± 0.002 | 0.013 ± 0.004 | 0.015 ± 0.001 |
| PAT | S | 1 | Ph | 0.065 ± 0.012 | 0.028 ± 0.005 | 0.071 ± 0.004 | 0.021 ± 0.001 | 0.028 ± 0.004 | 0.043 ± 0.005 |

Figure 7:
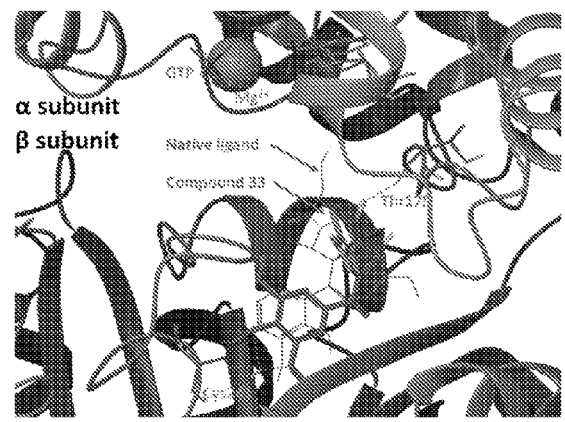
FIG. 7 depicts potential binding poses for compound 33 (tube model, Glide docking score of −8.70) and the native ligand DAMA-colchicine (thin wire model, Glide docking score of −9.26) in tubulin α,β-dimer (PDB Code: 1SA0).
Figure 8:
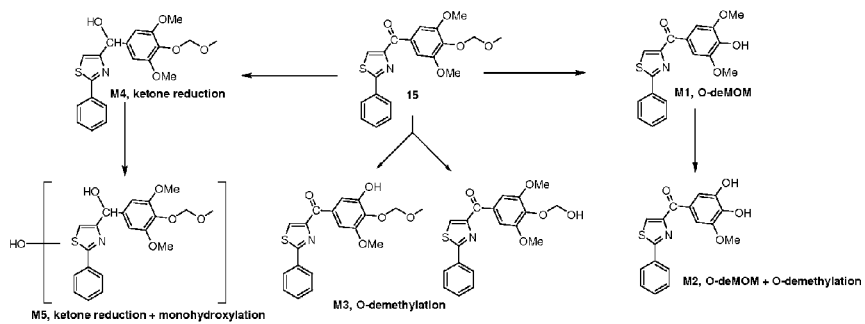
FIG. 8 presents proposed metabolites and metabolic pathway of compound 15.
Figure 9:
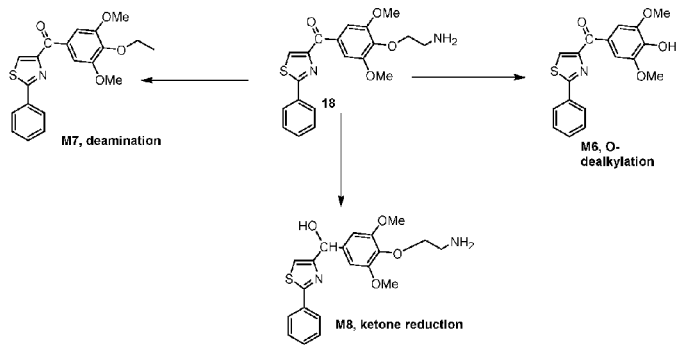
FIG. 9 presents proposed metabolites and metabolic pathway of compound 18.
Figure 10:
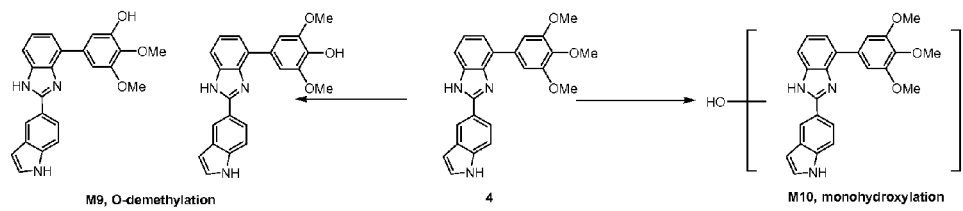
FIG. 10 presents proposed metabolites and metabolic pathway of compound 4.
Figure 11:
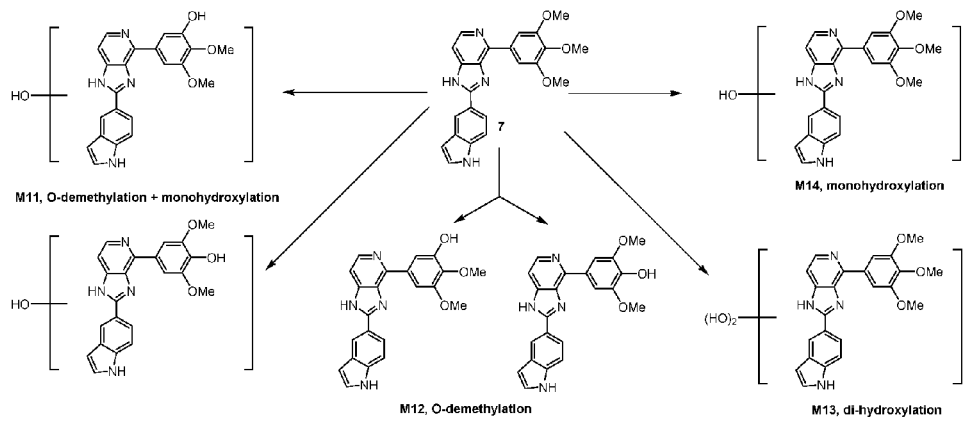
FIG. 11 presents proposed metabolites and metabolic pathway of compound 7.

Molecular modeling studies with 33 (FIG. 7) showed three hydrogen bonding interactions between this ligand and the tubulin α,β-dimer, similar to those observed between 4 or 7 and tubulin. However, the 5-indolyl moiety in compound 33 did not seem to reach the GTP moiety as in 4 or 7, possibly due to the fact that the ketone moiety was not forced into a ring system as seen in 4 or 7. Thus, 33 mainly stays within the β-subunit of tubulin dimer, and shows a slightly better Glide docking score (−8.70).

Example 6

Metabolic Stability Studies

Microsomal Stability Assay.
Metabolic stability studies were performed by incubating the test compounds (0.5 μM) in a total reaction volume of examine metabolic stability. The NADPH regenerating system (solution A and B) was obtained from Xenotech, LLC (Lenexa, Kans.). Aliquots (100 μL) from the reaction mixtures to determine metabolic stability were sampled at 5, 10, 20, 30, 60, and 90 min. Acetonitrile (200 μL) containing 200 nM of the internal standard was added to quench the reaction and to precipitate the proteins. Samples were then centrifuged at 10,000 rpm for 15 min at RT, and the supernatant was analyzed directly by LC-MS/MS (AB Sciex API4500). For metabolite identification, the reaction mixture was incubated for 2 h with 50 μM test compound concentration under the previously described conditions. The supernatants were analyzed using a Water Xevo G2-S high resolution mass spectrometer.

In Vitro Metabolic Stability Studies.
To determine whether the metabolism of the labile carbonyl linker may be reduced by incorporation into a cyclic structure, the metabolic stability was measured in liver microsomes for two potent compounds (4 and 7). The carbonyl linker in 10 was susceptible to ketone reduction was replaced by a ring. This modification preserved the potency while improving metabolic stability about 2-3 fold (17 min vs. 45 and 51 min in human liver microsomes, Table 4) compared to 10.

TABLE 4

Half-lives of tested compounds in liver microsomes of different species

| | $T_{1/2}$ (min) | | |
|---|---|---|---|
| Compounds | Human | Mouse | Rat |
| 4 | 50.7 ± 1.2 | 53.5 ± 2.4 | 72.3 ± 4.6 |
| 7 | 45.3 ± 2.0 | 19.7 ± 0.7 | 30.4 ± 1.9 |
| 15 | 7.8 ± 0.3 | 4.0 ± 0.3 | 9.7 ± 0.4 |
| 18 | 110.0 ± 5.5 | 123.0 ± 7.7 | 225.0 ± 12.6 |
| 10 | 17 | <<5 | 31 |

Furthermore, the potency of compounds 4 and 7 increased. Another active analogue 15 with an extended MOM tail at the para-benzoyl ring did not improve its metabolic stability in any of the tested liver microsomes. Another substituent, the aminoethyl of 18, at the same para-O position blocked the metabolic liability at the benzoyl ring ring ($T_{1/2}$ is 110~225 min over tested species liver microsomes). This result confirmed that para-position of the benzoyl ring could be a modifiable place for improvement of compound stability.

In Vitro Metabolic Pathways of Compounds 4, 7, 15, and 18.

In order to understand why these new analogues demonstrated different metabolic patterns in the liver microsomes, additional experiments were performed using a higher concentration (50 µM) of the tested compounds. We utilized a high resolution mass spectrometer for the identification of the metabolites with a mass error of less than 2 ppm generally. The detailed information regarding the mass spectrum and the chromatogram of each of the metabolites are presented in the supplementary materials. For 15 (FIG. 8), the removal of the MOM group to form M1 (identified by mass spectrum 342.08 [M+1]) is the major metabolic pathway, followed by O-demethylation of the 3'- or 5'-methoxy group to generate M2 (identified by mass spectrum 328.06 [M+1]). This result was consistent with the short half-life (<10 min) of this compound, as the MOM group seems to be unstable after exposure to liver microsomes. M3 (identified by mass spectrum 372.09 [M+1]) was also the 0-demethylation product, however, the exact site for this demethylation was not determined due to limited information available at this stage. M4 (identified by mass spectrum 388.12 [M+1]) was the product that resulted from ketone reduction and it was further hydroxylated to M5 (identified by mass spectrum 404.12 [M+1]) at a position that was unidentifiable due to limited information. For 18 (FIG. 9), M6 (de-alkylation) (identified by mass spectrum 342.08 [M+1]) and M8 (ketone reduction) (identified by mass spectrum 387.14 [M+1]) are the major metabolites. M7 (deamination) (identified by mass spectrum 370.11 [M+1]) was a minor product. For 4 (FIG. 10), O-demethylation (M9) and mono-hydroxylation (M10) were the major products. M9 (identified by mass spectrum 386.15 [M+1]) and M10 (identified by mass spectrum 416.16 [M+1]) had more than one possible structure as indicated in the chromatograms. For 7 (FIG. 11), various metabolites including O-demethylation (M12) (identified by mass spectrum 387.15 [M+1]), mono-hydroxylation (M14) (identified by mass spectrum 417.16 [M+1]), O-demethylation followed by mono-hydroxylation (M11) (identified by mass spectrum 403.14 [M+1]), and dihydroxylation (M13) (identified by mass spectrum 433.15 [M+1]) were detected. These products were formed very evenly with similar relative amount and all of these metabolites had multiple isomeric forms as indicated in the chromatograms.

Example 7

Inhibition of Tubulin Polymerization

In Vitro Tubulin Polymerization Assay.

Bovine brain tubulin (0.4 mg, >97% pure) (Cytoskeleton, Denver, Colo.) was mixed with 10 µM of the test compounds and incubated in 100 µl of general tubulin buffer (80 mM PIPES, 2.0 mM $MgCl_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, Vt.). The spectrophotometer was set at 37° C. for tubulin polymerization.

Compounds Inhibit In Vitro Tubulin Polymerization.

Figure 12:
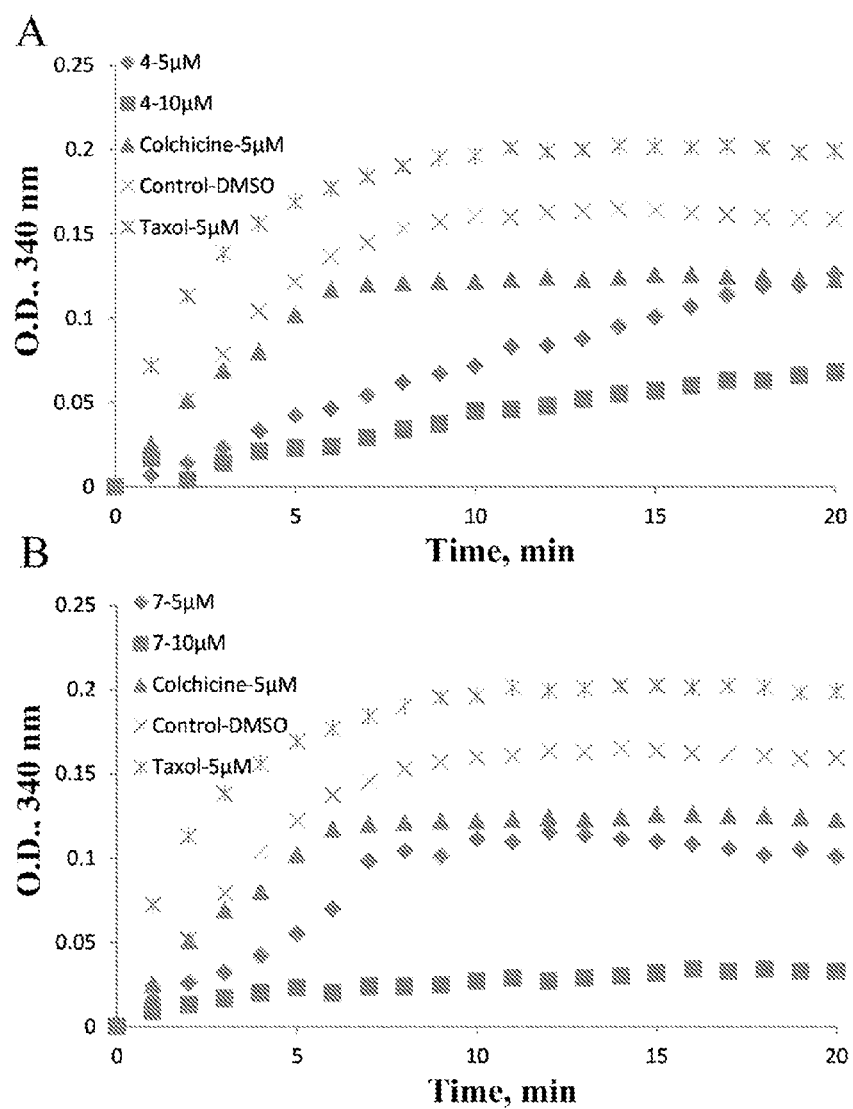
FIG. 12 compounds 4 and 7 inhibit tubulin polymerization in vitro.

The inhibition of tubulin polymerization of selected potent 4 and 7 with improved metabolic properties was studied and compared with positive control colchicine and negative control taxol. DMSO was used as a blank control. Bovine brain tubulin (>97% pure) was incubated with the individual compounds (5 or 10 µM) to test their effect on tubulin polymerization (FIG. 12). After 20 min incubation, tubulin polymerization was inhibited to the extent of 30% and 60% by 4 at 5 and 10 µM, respectively (FIG. 12A), as compared to vehicle. While about 33% and 81% inhibition was observed for 7 at 5 and 10 µM, respectively (FIG. 12B). Both 4 and 7 showed stronger inhibition than colchicine at the two tested concentrations. These data suggested that these compounds exhibit strong anti-tubulin polymerization activity that corresponds well with their cytotoxicity.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound represented by formula II:

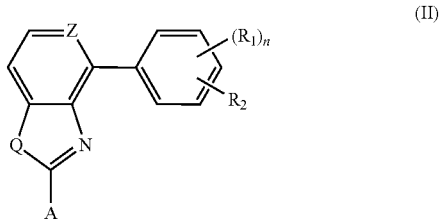

wherein

Q is S, NH, or O;

Z is CH or N;

A is substituted or unsubstituted phenyl; substituted or unsubstituted indolyl; or substituted or unsubstituted indazolyl;

wherein the optional substituents of A include O-alkyl, O-haloalkyl, F, Cl, Br, I, NO$_2$, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, —SO$_2$-aryl, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or a combination thereof;

R$_1$ is independently hydrogen, O-alkyl, O-haloalkyl, F, Cl, Br, I, haloalkyl, CF$_3$, CN, NO$_2$, —CH$_2$CN, NH$_2$, hydroxyl, COOH, C(O)H, NHCO-alkyl, —O(CH$_2$)$_j$OCH$_3$, —O(CH$_2$)$_j$OH, -O(CH$_2$)$_j$NHCH$_3$, —O(CH$_2$)$_j$NH$_2$, —O—(CH$_2$)$_j$N(CH$_3$)$_2$, —OC(O)CF$_3$, —OC(O)CH$_2$Cl, —OCH$_2$Ph, —O(CH$_2$)$_j$NH$_2$, —O(CH$_2$)$_j$N-phthalimide or a combination thereof;

R$_2$ is hydrogen, O-alkyl, O-haloalkyl, F, Cl, Br, I, haloalkyl, CF$_3$, CN, NO$_2$, —CH$_2$CN, NH$_2$, hydroxyl, COOH, C(O)H, NHCO-alkyl, —O(CH$_2$)$_k$OCH$_3$, —O(CH$_2$)$_k$OH, —O(CH$_2$)$_k$NHCH$_3$, —O(CH$_2$)$_k$NH$_2$, —O—(CH$_2$)$_k$N(CH$_3$)$_2$, —OC(O)CF$_3$, —OC(O)CH$_2$Cl, —OCH$_2$Ph, —O(CH$_2$)$_k$NH$_2$ or —O(CH$_2$)$_k$N-phthalimide;

i, j, and k are independently an integer between 0 to 5;

n is an integer between 1 to 4;

or a metabolite, hydrate, isomer, N-oxide, prodrug, pharmaceutical product, pharmaceutically acceptable salt, polymorph, tautomer, or a combination thereof.

2. The compound of claim 1, wherein R$_1$ is OCH$_3$, n is 3 and R$_2$ is hydrogen.

3. The compound of claim 1, or a pharmaceutically acceptable salt thereof, wherein said compound is compound 3 represented by the structure:

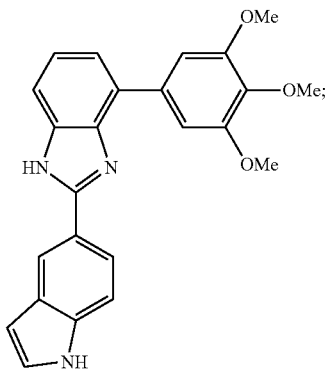

3

4. The compound of claim 1, or a pharmaceutically acceptable salt thereof, wherein said compound is compound 4, 5, 6 or 7:

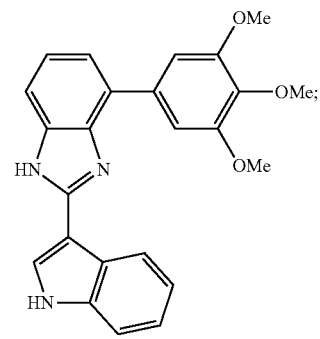

4

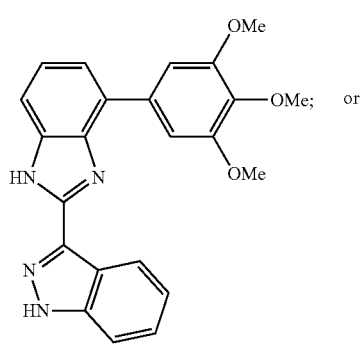

5

6 or

7

5. A pharmaceutical composition comprising a compound according to claim 1, or a pharmaceutically acceptable salt thereof, and at least one pharmaceutically acceptable carrier.

6. The pharmaceutical composition of claim 5, further comprising at least one other anti-cancer agent in addition to the compound of Formula II.

7. The compound of claim 1, wherein said compound has the formula (VII):

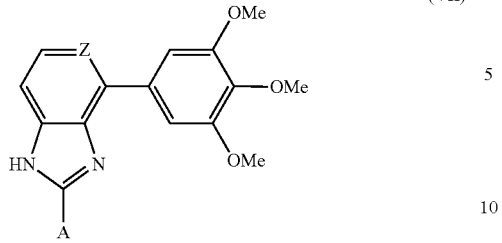

(VII)

wherein

Z is CH or N;

A is substituted or unsubstituted phenyl; substituted or unsubstituted indolyl; or substituted or unsubstituted indazolyl;

wherein the optional substituents of A are selected from the group consisting of O-alkyl, O-haloalkyl, F, Cl, Br, I, $NO_2$, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, —$SO_2$-aryl, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ and combinations thereof;

i is an integer between 0 to 5;

or a metabolite, hydrate, isomer, N-oxide, prodrug, pharmaceutical product, pharmaceutically acceptable salt, polymorph, tautomer, or a combination thereof.

\* \* \* \* \*